(12) United States Patent
Himmler et al.

(10) Patent No.: US 12,006,327 B2
(45) Date of Patent: Jun. 11, 2024

(54) PROCESS FOR PREPARING SUBSTITUTED CYCLOHEXANE AMINO ACID ESTERS AND SPIROKETAL-SUBSTITUTED CYCLIC KETO-ENOLS

(71) Applicant: Bayer Aktiengesellschaft, Leverkusen (DE)

(72) Inventors: Thomas Himmler, Odenthal (DE); Peter Bruechner, Krefeld (DE); Werner Lindner, Cologne (DE); Julia Johanna Hahn, Duesseldorf (DE); Wahed Ahmed Moradi, Monheim (DE); Reiner Fischer, Monheim (DE); Michael Dockner, Cologne (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 454 days.

(21) Appl. No.: 17/046,156

(22) PCT Filed: Apr. 3, 2019

(86) PCT No.: PCT/EP2019/058354
§ 371 (c)(1),
(2) Date: Oct. 8, 2020

(87) PCT Pub. No.: WO2019/197231
PCT Pub. Date: Oct. 17, 2019

(65) Prior Publication Data
US 2021/0032262 A1   Feb. 4, 2021

(30) Foreign Application Priority Data

Apr. 10, 2018 (EP) .................... 18166442

(51) Int. Cl.
| | | |
|---|---|---|
| C07D 491/113 | (2006.01) | |
| C07C 229/48 | (2006.01) | |
| C07C 233/52 | (2006.01) | |
| C07D 209/54 | (2006.01) | |

(52) U.S. Cl.
CPC ........ *C07D 491/113* (2013.01); *C07C 229/48* (2013.01); *C07C 233/52* (2013.01); *C07D 209/54* (2013.01); *C07C 2601/14* (2017.05); *C07C 2601/16* (2017.05)

(58) Field of Classification Search
CPC .................................................. C07D 491/113
See application file for complete search history.

(56) References Cited

U.S. PATENT DOCUMENTS

| | | | |
|---|---|---|---|
| 6,589,976 B1 | 7/2003 | Fischer et al. | |
| 8,138,119 B2 | 3/2012 | Fischer et al. | |
| 8,410,289 B2 | 4/2013 | Fischer et al. | |
| 2006/0292073 A1* | 12/2006 | Goodman | A61K 51/0402 548/953 |
| 2008/0305955 A1* | 12/2008 | Bretschneider | A01N 43/38 544/70 |
| 2011/0086762 A1* | 4/2011 | Fischer | C07D 491/113 514/409 |
| 2011/0190493 A1 | 8/2011 | Bretschneider et al. | |
| 2019/0202837 A1* | 7/2019 | Himmler | C07D 491/113 |

FOREIGN PATENT DOCUMENTS

| | | | | |
|---|---|---|---|---|
| EP | 3301092 A2 | 4/2018 | | |
| TW | 200612823 A | 5/2006 | | |
| TW | 200808721 A | 2/2008 | | |
| WO | 9916748 A1 | 4/1999 | | |
| WO | 2006000355 A1 | 1/2006 | | |
| WO | 2006089633 A3 | 11/2006 | | |
| WO | 2007048545 A2 | 5/2007 | | |
| WO | 2007096058 A1 | 8/2007 | | |
| WO | 2014024659 A1 | 2/2014 | | |
| WO | 2018/024659 A1 | 2/2018 | | |
| WO | WO-2018024659 A1 * | 2/2018 | ........... | C07D 317/72 |

OTHER PUBLICATIONS

International Search Report for Application No. PCT/EP2019/058354 dated May 22, 2019.

* cited by examiner

*Primary Examiner* — Matthew P Coughlin
(74) *Attorney, Agent, or Firm* — McBee Moore & Vanik, IP, LLC

(57) ABSTRACT

The present invention relates to a novel process for preparing substituted cyclohexane amino acid esters and spiroketal-substituted cyclic keto-enols, and to novel intermediates or starting compounds that are passed through or used in the process according to the invention.

7 Claims, No Drawings

PROCESS FOR PREPARING SUBSTITUTED CYCLOHEXANE AMINO ACID ESTERS AND SPIROKETAL-SUBSTITUTED CYCLIC KETO-ENOLS

CROSS-REFERENCE TO RELATED APPLICATIONS

This application is the National Stage entry of International Application No. PCT/EP2019/058354, filed 3 Apr. 2019, which claims priority to European Patent Application No. 18166442.6, filed 10 Apr. 2018.

BACKGROUND

Field

The present invention relates to a novel process for preparing substituted cyclohexane amino acid esters and spiroketal-substituted cyclic keto-enols, and to novel intermediates or starting compounds that are passed through or used in the process according to the invention. Substituted cyclic cyclohexane amino acid esters are important intermediates for synthesis of active insecticidal, acaricidal and herbicidal ingredients.

Description of Related Art

It is already known that certain spiroketal-substituted cyclic keto-enols have insecticidal, acaricidal or herbicidal activity (WO 99/16748; WO 06/089633). One known synthesis (A) (WO 2014/024659) of such spiroketal-substituted cyclic keto-enols proceeds from correspondingly spiroketal-substituted cyclohexanones of the general formula (I), which are converted in a Bucherer-Bergs reaction to the spiroketal-substituted hydantoins of the general formula (II). Alkaline hydrolysis of these hydantoins affords the spiroketal-substituted cyclohexane amino acids of the general formula (III). These amino acids are then esterified by reaction with methanol and thionyl chloride to give a mixture of the hydrochlorides of the substituted cyclohexane amino acid methyl esters of the general formulae (IV), (V) and (VI). By means of bases, these hydrochlorides can be used to obtain the free cyclohexane amino acid methyl esters of the general formulae (IV), (V) and (VI). These amino acid methyl esters are then acylated at the nitrogen with phenylacetyl chlorides of the general formula (VII) to give a mixture of the compounds of the general formulae (VIII), (IX) and (X). The compounds of the general formulae (VIII), (IX) and (X) are then cyclized in a Dieckmann reaction by action of a strong base such as potassium tert-butoxide or sodium methoxide to give a mixture of the substituted cyclic keto-enols of the general formulae (XI), (XII) and (XIII). In a last step, these compounds are then converted by reaction with an α,ω-diol of the general formula (XIV) to the compound of the general formula (XI). This process (A) is shown in Scheme 1. A considerable disadvantage of this process (A) is that the esterification of the amino acids of the general formula (III) with methanol/thionyl chloride also results in formation of methyl chloride. Owing to its low boiling point (−24° C.), methyl chloride escapes with the offgas. Its disposal (for example by combustion) can constitute a major technical problem.

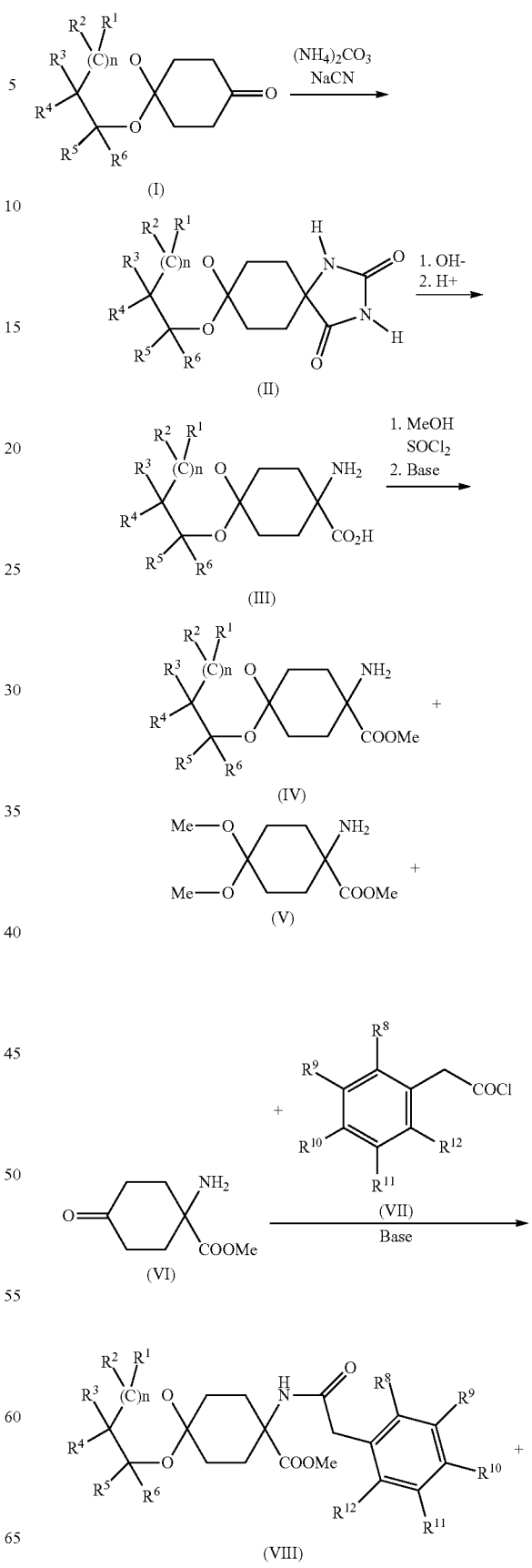

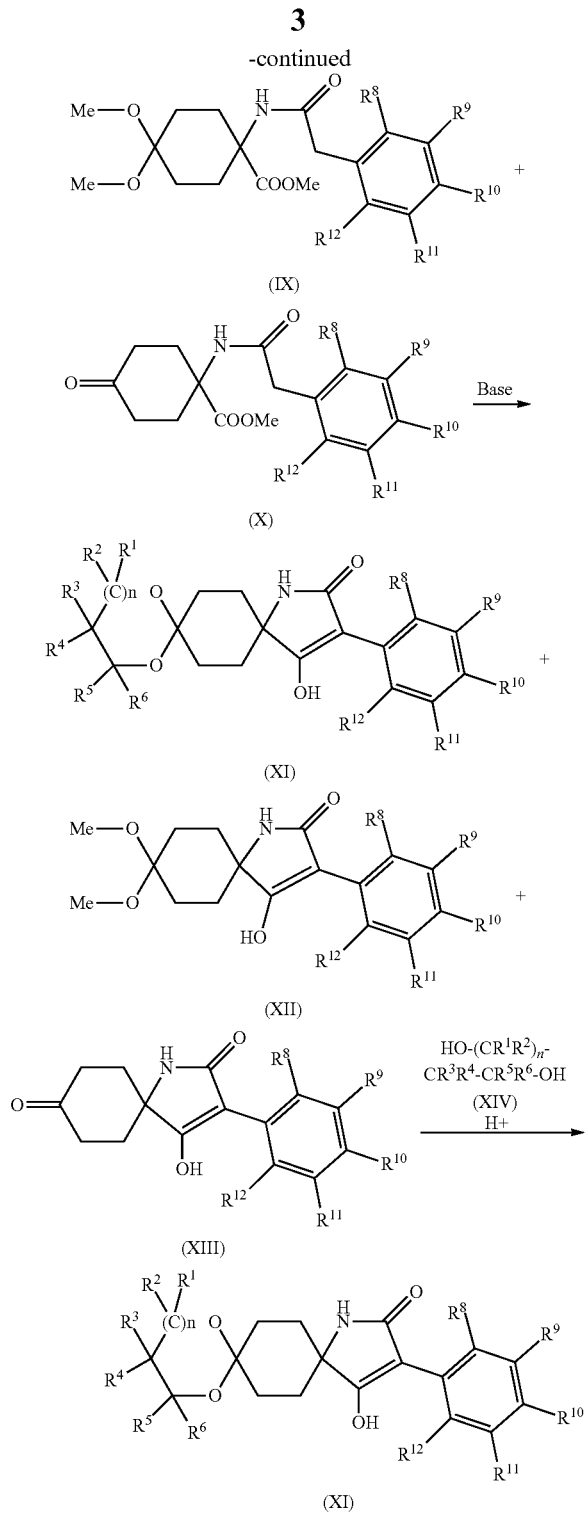

SUMMARY

It has now been found that the synthesis of spiroketal-substituted cyclohexane amino acid esters of the general formula (VIII) and of spiroketal-substituted cyclic keto-enols of the general formula (XI) can be simplified by using higher alcohols rather than methanol, the corresponding alkyl chlorides of which, owing to their higher boiling points, can more easily be removed from the offgas stream by technical methods that are known in principle, or no longer occur therein. It has also been found that, surprisingly, in the reaction with higher alcohols than methanol, the formation of the dialkyl acetals is distinctly reduced. This simplifies the reaction sequence and shortens the last step of the process.

A first embodiment (process B) of the process according to the invention is characterized in that spiroketal-substituted cyclohexane amino acids of the general formula (III) are esterified by reaction with an alcohol of the general formula (XV)

$$R^7\text{—OH} \qquad\qquad (XV)$$

in which $R^7$ is optionally branched $C_2$-$C_8$-alkyl, and thionyl chloride to give mixtures of the hydrochlorides of the spiroketal-substituted cyclohexane amino acid esters of the general formula (IV'), dialkylketal-substituted cyclohexane amino acid esters of the general formula (V') and 4-cyclohexanone amino acid esters of the general formula (VI'). By means of bases, these hydrochlorides can be used to obtain the free spiroketal-substituted cyclohexane amino acid esters of the general formula (IV'), dialkylketal-substituted cyclohexane amino acid esters of the general formula (V') and 4-cyclohexanone amino acid esters of the general formula (VI'). These amino acid esters are then acylated at the nitrogen in the presence of a base with phenylacetyl chlorides of the general formula (VII) to give mixtures of the compounds of the general formulae (VIII'), (IX') and (X'). These compounds are subsequently cyclized in a Dieckmann reaction by action of a strong base such as potassium tert-butoxide or sodium methoxide to give mixtures of the compounds of the general formulae (XI), (XII') and (XIII). Finally, these compounds are then converted by reaction in the presence of an acid with an α,ω-diol of the general formula (XIV)

$$\text{HO—}(CR^1R^2)_n\text{—}CR^3R^4\text{—}CR^5R^6\text{—OH} \qquad\qquad (XIV)$$

in which $R^1$ to $R^6$ are independently hydrogen, methyl, ethyl or phenyl, and n is 0 or 1, to a single spiroketal-substituted keto-enol of the general formula (XI).

The process (B) according to the invention is depicted in Scheme 2.

In the general formulae (I), (II), (III), (IV), (V), (VI), (VII), (VIII), (IX), (X), (XI), (XII), (XIII) and (XIV), $R^1$, $R^2$, $R^3$, $R^4$, $R^5$, $R^6$, $R^8$, $R^9$, $R^{10}$, $R^{11}$, $R^{12}$ and n have the definitions given below.

There was therefore still a need for a process having better performability under industrial conditions for preparing spiroketal-substituted cyclohexane amino acid esters of the general formula (VIII) and spiroketal-substituted cyclic keto-enols of the general formula (XI).

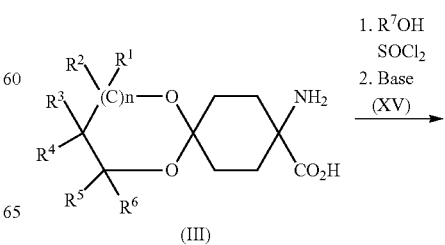

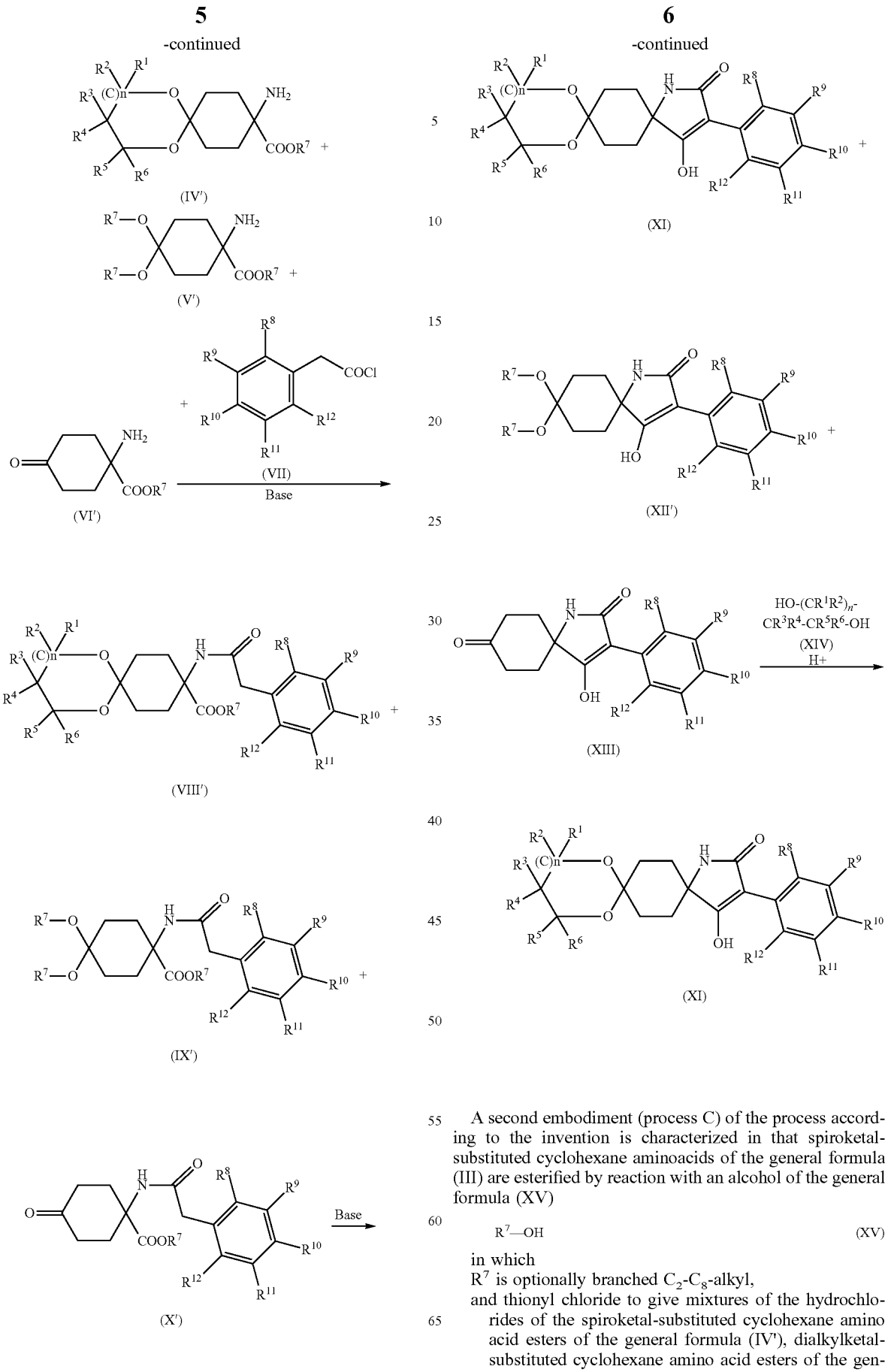

A second embodiment (process C) of the process according to the invention is characterized in that spiroketal-substituted cyclohexane aminoacids of the general formula (III) are esterified by reaction with an alcohol of the general formula (XV)

R⁷—OH     (XV)

in which
R⁷ is optionally branched $C_2$-$C_8$-alkyl,
and thionyl chloride to give mixtures of the hydrochlorides of the spiroketal-substituted cyclohexane amino acid esters of the general formula (IV'), dialkylketal-substituted cyclohexane amino acid esters of the general formula (V') and 4-cyclohexanone amino acid esters of the general formula (VI'). By means of bases, these hydrochlorides can be used to obtain the free spiroketal-substituted cyclohexane amino acid esters of the general formula (IV'), dialkylketal-substituted cyclohexane amino acid esters of the general formula (V') and 4-cyclohexanone amino acid esters of the general formula (VI'). These amino acid esters are then acylated at the nitrogen in the presence of a base with phenylacetyl chlorides of the general formula (VII) to give mixtures of the compounds of the general formulae (VIII'), (IX') and (X'). These compounds are then converted by reaction in the presence of an acid with an α,ω-diol of the general formula (XIV)

HO—(CR¹R²)$_n$—CR³R⁴—CR⁵R⁶—OH        (XIV)

in which

R¹ to R⁶ are independently hydrogen, methyl, ethyl or phenyl, and n is 0 or 1, to the homogeneously spiroketal-substituted compound of the general formula (XVI)

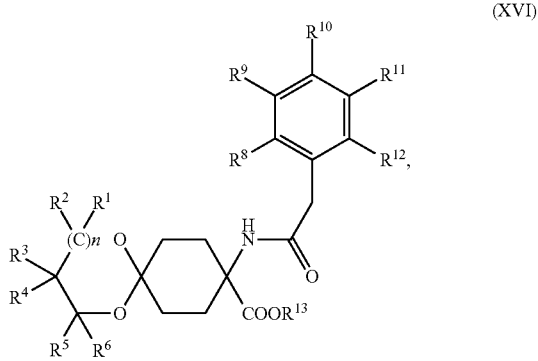

in which

R¹³ is optionally branched $C_2$-$C_8$-alkyl or —(CR¹R²)$_n$—CR³R⁴—CR⁵R⁶—OH.

Finally, the compound of the formula (XVI) is then cyclized in a Dieckmann reaction by action of a strong base (for example potassium tert-butoxide or sodium methoxide) to give the compound of the formula (XI).

The process (C) according to the invention is depicted in Scheme 3.

Scheme 3: Process C according to the invention

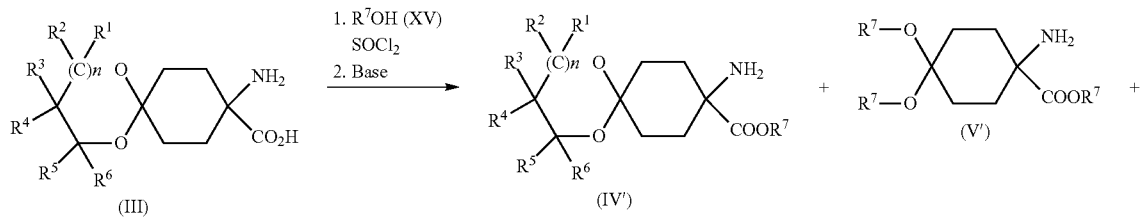

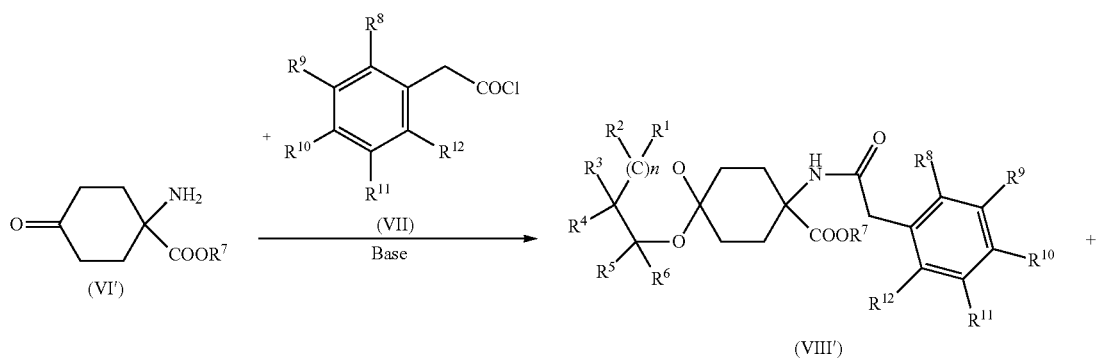

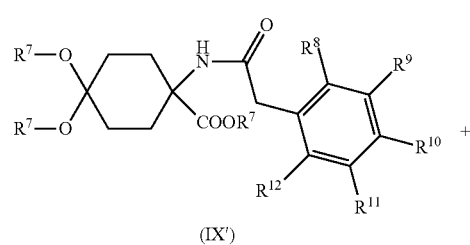

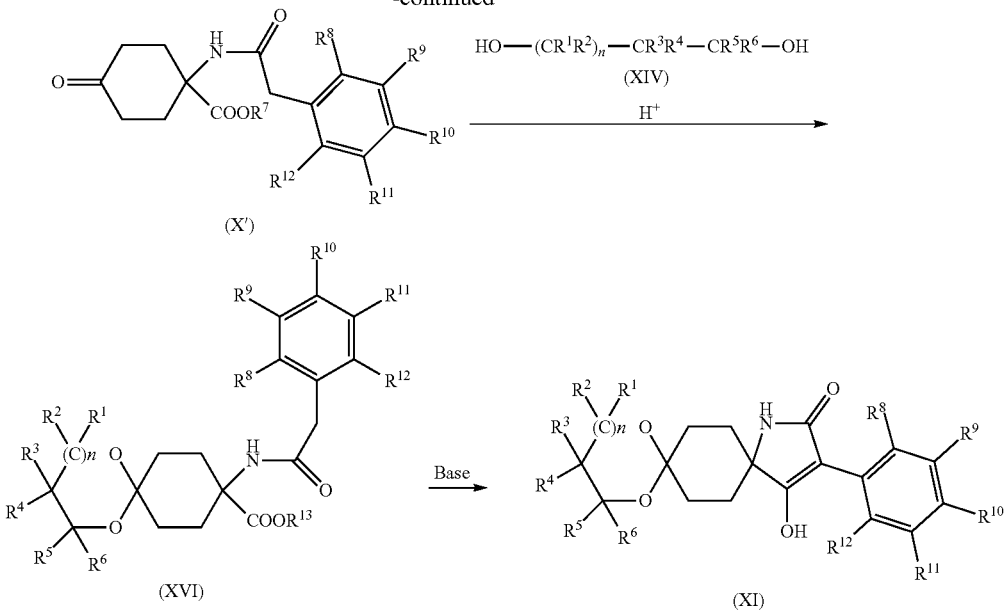

In the general formulae (III), (IV'), (V'), (VI), (VII), (VIII'), (IX'), (X'), (XI), (XII'), (XIII), (XIV), (XV) and (XVI), $R^1$ to $R^6$ are independently hydrogen, methyl, ethyl or phenyl, $R^7$ is optionally branched $C_2$-$C_8$-alkyl, $R^8$ to $R^{12}$ are independently hydrogen, methyl, ethyl, fluoroalkyl having one or 2 carbon atoms and one to five fluorine atoms, halogen, methoxy, ethoxy, trifluoromethoxy or optionally methyl-, ethyl-, methoxy-, ethoxy- or halogen-substituted phenyl, $R^{13}$ is optionally branched $C_2$-$C_8$-alkyl or —$(CR^1R^2)_n$—$CR^3R^4$—$CR^5R^6$—OH, n is 0 or 1.

DETAILED DESCRIPTION OF A PREFERRED EMBODIMENT

Preferably, $R^1$ to $R^6$ are independently hydrogen, methyl or ethyl, $R^7$ is ethyl, n-propyl, i-propyl, n-butyl or n-hexyl, $R^8$ to $R^{12}$ are independently hydrogen, methyl, ethyl, fluorine, chlorine, bromine, methoxy, ethoxy, trifluoromethoxy or optionally methyl-, ethyl-, methoxy-, ethoxy-, fluorine-, chlorine- or bromine-substituted phenyl, $R^{13}$ is ethyl, n-propyl, i-propyl, n-butyl, n-hexyl or —$(CR^1R^2)_n$—$CR^3R^4$—$CR^5R^6$—OH, n is 0 or 1.

More preferably, $R^3$ to $R^6$ are independently hydrogen or methyl, $R^7$ is ethyl, n-propyl, i-propyl, n-butyl or n-hexyl, $R^8$ to $R^{12}$ are independently hydrogen, methyl, ethyl, fluorine, chlorine, bromine, methoxy, ethoxy or optionally methyl-, methoxy-, fluorine- or chlorine-substituted phenyl, $R^{13}$ is ethyl, n-propyl, i-propyl, n-butyl, n-hexyl or —$(CR^1R^2)_n$—$CR^3R^4$—$CR^5R^6$—OH, n is 0.

Most preferably, $R^3$ is hydrogen, $R^4$ is hydrogen or methyl, $R^5$ is hydrogen, $R^6$ is hydrogen or methyl, $R^7$ is ethyl, n-propyl, i-propyl, n-butyl or n-hexyl, $R^8$ is hydrogen, methyl, ethyl, methoxy, ethoxy, chlorine or bromine, $R^9$ is hydrogen, $R^{10}$ is hydrogen, methyl, chlorine or bromine, $R^{11}$ is hydrogen, $R^{12}$ is hydrogen, methyl, ethyl, methoxy, ethoxy, chlorine or bromine, $R^{13}$ is ethyl, n-propyl, i-propyl, n-butyl, n-hexyl or —$(CR^1R^2)_n$—$CR^3R^4$—$CR^5R^6$—OH, n is 0.

Especially preferably, $R^3$ is hydrogen, $R^4$ is hydrogen, $R^5$ is hydrogen, $R^6$ is hydrogen, $R^7$ is ethyl, n-propyl or n-butyl, $R^8$ is methyl, ethyl, chlorine or bromine, $R^9$ is hydrogen, $R^{10}$ is hydrogen, chlorine or bromine, $R^{11}$ is hydrogen, $R^{12}$ is methyl, ethyl, chlorine or bromine, $R^{13}$ is ethyl, n-propyl, n-butyl or —$(CR^1R^2)_n$—$CR^3R^4$—$CR^5R^6$—OH, n is 0.

Exceptionally preferably, $R^3$ is hydrogen, $R^4$ is hydrogen, $R^5$ is hydrogen, $R^6$ is hydrogen, $R^7$ is ethyl, n-propyl or n-butyl, $R^8$ is methyl, $R^9$ is hydrogen, $R^{10}$ is chlorine, $R^{11}$ is hydrogen, $R^{12}$ is methyl,
$R^{13}$ is ethyl, n-propyl, n-butyl or —$(CR^1R^2)_n$—$CR^3R^4$—$CR^5R^6$—OH,
n is 0.

Likewise exceptionally preferably,
$R^3$ is hydrogen,
$R^4$ is hydrogen,
$R^5$ is hydrogen,
$R^6$ is hydrogen,
$R^7$ is n-propyl,
$R^8$ is methyl,
$R^9$ is hydrogen,
$R^{10}$ is chlorine,
$R^{11}$ is hydrogen,
$R^{12}$ is methyl,
$R^{13}$ is n-propyl or —$CH_2CH_2$—OH,
n is 0.

$R^1$ to $R^6$ is $R^1$, $R^2$, $R^3$, $R^4$, $R$, $R^6$.
$R^8$ to $R^{12}$ is $R^8$, $R^9$, $R^{10}$, $R^{11}$, $R^{12}$.

There follows a detailed elucidation of process (B) according to the invention.

First step (1) of process (B) according to the invention: The reaction of compounds of the general formula (III) with an alcohol of the general formula (XV) and thionyl chloride to give the hydrochlorides of the compounds of the general formulae (IV'), (V') and (VI') can be conducted without diluent or optionally in the presence of an inert diluent, for example toluene, chlorobenzene, 1,2-dichlorobenzene, heptane, isooctane, methylcyclohexane, anisole or acetonitrile. Preference is given to working without diluent, meaning that the alcohol used for esterification is used in excess as diluent.

The amount of thionyl chloride can be varied within wide limits. Typically, 0.5 to 5 molar equivalents of thionyl chloride are employed, based on compound of the general formula (III). Preference is given to using 0.9 to 3 molar equivalents of thionyl chloride. Particular preference is given to using 1.2 to 3 molar equivalents of thionyl chloride.

The reaction temperature is between −10 and 150° C., preferably between 0 and 120° C.

The reaction can in principle also be conducted under reduced or elevated pressure.

The workup can be effected, for example, by distillative removal of the alcohol and excess thionyl chloride. In this way, the hydrochlorides of the compounds of the general formulae (IV'), (V') and (VI') are obtained, which can be used as such in the next step of process (B) according to the invention.

However, it is also possible to convert the hydrochlorides of the compounds of the general formulae (IV'), (V') and (VI'), by addition of a base, to the free amino ester compounds of the general formulae (IV'), (V') and (VI') and to isolate these by customary workup methods such as filtration or extraction.

Bases used may be inert inorganic and organic bases, for example sodium carbonate, sodium hydrogencarbonate, potassium carbonate, potassium hydrogencarbonate, lithium hydroxide, sodium hydroxide, potassium hydroxide, ammonia, triethylamine, tributylamine, pyridine or 2-methyl-5-ethylpyridine or mixtures of these bases. Preference is given to using sodium carbonate. Preference is likewise given to using the mixture of sodium carbonate with sodium hydroxide.

The amount of base is chosen such that the proportion of hydrochloride (HCl) in the mixture of the hydrochlorides of the compounds of the general formulae (IV'), (V') and (VI') is neutralized.

Second step (2) of process (B) according to the invention: The hydrochlorides of the compounds of the general formulae (IV'), (V') and (VI') or the compounds of the general formulae (IV'), (V') and (VI') are reacted in the presence of an inert diluent and a base with an acid chloride of the general formulae (VII) to give compounds of the general formulae (VIII'), (IX') and (X').

Diluents used may, for example, be dichloromethane, toluene, xylene, chlorobenzene, 1,2-dichlorobenzene, heptane, isooctane, methylcyclohexane, tetrahydrofuran, ethyl acetate, acetonitrile, anisole or butyronitrile. Preference is given to using tetrahydrofuran (THF), anisole, toluene, xylene, chlorobenzene or acetonitrile. Particular preference is given to using toluene, chlorobenzene or anisole.

Bases used may be inorganic or organic bases. Examples here include: sodium hydroxide, potassium hydroxide, sodium carbonate, sodium hydrogencarbonate, potassium carbonate, potassium hydrogencarbonate, triethylamine, tributylamine, morpholine, piperidine, pyridine, 2-methyl-5-ethylpyridine or mixtures of these bases. Preference is given to using sodium carbonate or potassium carbonate. Particular preference is given to using sodium carbonate. Particular preference is likewise given to using the mixture of sodium carbonate with sodium hydroxide.

The amount of base is guided by whether the hydrochlorides of the compounds of the general formulae (IV'), (V') and (VI') or the compounds of the general formulae (IV'), (V') and (VI') are being used. If the hydrochlorides of the compounds of the general formulae (IV'), (V') and (VI') are used, at least two molar equivalents of base will be used in order to convert the hydrochlorides in situ to the free compounds of the general formulae (IV'), (V') and (VI') and then to conduct the acylation reaction. If, by contrast, the free compounds of the general formulae (IV'), (V') and (VI') are used directly, at least one molar equivalent of base is used.

The acid chloride of the general formula (VII) can be used in any desired molar ratios based on the mixture of the compounds (IV'), (V') and (VI'). Typically between 0.9 and 2 molar equivalents of acid chloride are used, preferably between 0.95 and 1.3 molar equivalents.

The reaction temperature is between −10 and 120° C., preferably between 0 and 100° C.

The reaction can in principle also be conducted under reduced or elevated pressure.

The workup is effected by known methods in organic chemistry, for example by filtration or extraction.

Third step (3) of process (B) according to the invention: The compounds of the general formulae (VIII'), (IX') and (X') are converted in the presence of an inert diluent and a strong base to the compounds of the general formulae (XI), (XII') and (XIII).

Examples of useful diluents include: toluene, ortho-, meta- or para-xylene, mesitylene, chlorobenzene, ortho-dichlorobenzene, anisole, acetonitrile, butyronitrile, tetrahydrofuran, 2-methyltetrahydrofuran, cyclopentyl methyl ether, methyl tert-butyl ether, tert-amyl methyl ether, 1,4-dioxane, N,N-dimethylformamide, N,N-dimethylacetamide, N-methylpyrrolidone, methanol, ethanol, 1-butanol, tert-butanol or mixtures of these solvents. Preference is given to N,N-dimethylformamide, N,N-dimethylacetamide (DMAc), N-methylpyrrolidone (NMP), methanol, tert-butanol, chlorobenzene, ortho-dichlorobenzene, anisole or mixtures of these solvents. Particular preference is given to DMAc, NMP, toluene, chlorobenzene and anisole.

Bases used may, for example, be sodium hydroxide, potassium hydroxide, sodium methoxide, potassium methoxide, sodium ethoxide, potassium ethoxide, sodium tert-butoxide or potassium tert-butoxide. Preference is given to sodium methoxide and potassium tert-butoxide. Particular preference is given to using sodium methoxide.

The bases are employed in an amount of from 0.9 to 4 molar equivalents, based on the compounds of the general formulae (VIII'), (IX') and (X'). Preference is given to using 1 to 3.5 molar equivalents.

The temperature is between 20 and 170° C. Preference is given to working between 40 and 150° C.

After the pH of the reaction mixture has been adjusted to a value between 0 and 8, the compounds of the general formulae (XI), (XII') and (XIII) are isolated by known customary methods in organic chemistry such as filtration, phase separation or extraction.

Fourth step (4) of process (B) according to the invention: The mixture of the compounds of the general formulae (XI), (XII') and (XIII) is reacted in the presence of an inert diluent and an acid with an $\alpha,\overline{\omega}$-diol of the general formula (XIV) to give the compound of the general formula (XI).

Examples of useful diluents include: dichloromethane, toluene, ortho-, meta- or para-xylene, mesitylene, chlorobenzene, ortho-dichlorobenzene, acetonitrile, butyronitrile, tetrahydrofuran, 2-methyltetrahydrofuran, cyclopentyl methyl ether, methyl tert-butyl ether, tert-amyl methyl ether, 1,4-dioxane, anisole or mixtures of these solvents. Preference is given to toluene, ortho-, meta- or para-xylene, chlorobenzene, acetonitrile, butyronitrile, 2-methyltetrahydrofuran, cyclopentyl methyl ether, methyl tert-butyl ether, tert-amyl methyl ether or mixtures of these solvents.

The $\alpha,\overline{\omega}$-diol of the general formula (XIV) is used in an amount of at least 1 mol based on 1 mol of the compounds of the general formulae (XII') and (XIII). It is also possible to work in any excess of $\alpha,\overline{\omega}$-diol of the general formula (XIV) and hence to simultaneously use it as solvent.

The fourth stage of the process according to the invention is conducted in the presence of a catalytic amount of an acid. Possible acids include, for example: hydrogen chloride, sulfuric acid, methanesulfonic acid, trifluoromethanesulfonic acid, para-toluenesulfonic acid or acidic ion exchange resins such as, for example, Amberlite. Preference is given to using sulfuric acid or para-toluenesulfonic acid. Particular preference is given to using sulfuric acid.

The acid is used in amounts of 0.01 to 20 percent by weight, based on the compounds of the general formulae (XII') and (XIII). Preference is given to 0.05 to 10 percent by weight.

The fourth stage of the process according to the invention is conducted at temperatures between 20 and 150° C.; preferably between 50 and 120° C.

To attain maximum conversion, it may be advantageous to remove the water of reaction formed, for example by distillation.

The compounds of the general formula (XI) are isolated by known customary methods in organic chemistry such as filtration, phase separation or extraction.

There follows a detailed elucidation of process (C) according to the invention.

First step (1) of process (C) according to the invention: The reaction of compounds of the general formula (III) with an alcohol of the general formula (XV) and thionyl chloride to give the hydrochlorides of the compounds of the general formulae (IV'), (V') and (VI') can be conducted without diluent or optionally in the presence of an inert diluent, for example toluene, chlorobenzene, 1,2-dichlorobenzene, heptane, isooctane, methylcyclohexane, anisole or acetonitrile.

Preference is given to working without diluent, meaning that the alcohol used for esterification is used in excess as diluent.

The amount of thionyl chloride can be varied within wide limits. Typically, 0.5 to 5 molar equivalents of thionyl chloride are employed, based on compound of the general formula (III). Preference is given to using 0.9 to 3 molar equivalents of thionyl chloride. Particular preference is given to using 1.2 to 3 molar equivalents of thionyl chloride.

The reaction temperature is between −10 and 150° C., preferably between 0 and 120° C.

The reaction can in principle also be conducted under reduced or elevated pressure.

The workup can be effected, for example, by distillative removal of the alcohol and excess thionyl chloride. In this way, the hydrochlorides of the compounds of the general formulae (IV'), (V') and (VI') are obtained, which can be used as such in the next step of process (C) according to the invention.

However, it is also possible to convert the hydrochlorides of the compounds of the general formulae (IV'), (V') and (VI'), by addition of a base, to the free amino acid compounds of the general formulae (IV'), (V') and (VI') and to isolate these by customary workup methods such as filtration or extraction.

Bases used may be inert inorganic and organic bases, for example sodium carbonate, sodium hydrogencarbonate, potassium carbonate, potassium hydrogencarbonate, lithium hydroxide, sodium hydroxide, potassium hydroxide, ammonia, triethylamine, tributylamine, pyridine or 2-methyl-5 ethylpyridine or mixtures of these bases. Preference is given to using sodium carbonate. Preference is likewise given to using the mixture of sodium carbonate with sodium hydroxide.

The amount of base is chosen such that the proportion of hydrochloride (HCl) in the mixture of the hydrochlorides of the compounds of the general formulae (IV'), (V') and (VI') is neutralized.

Second step (2) of process (C) according to the invention: The hydrochlorides of the compounds of the general formulae (IV'), (V') and (VI') or the compounds of the general formulae (IV'), (V') and (VI') are reacted in the presence of an inert diluent and a base with an acid chloride of the general formulae (VII) to give compounds of the general formulae (VIII'), (IX') and (X').

Diluents used may, for example, be dichloromethane, toluene, xylene, chlorobenzene, 1,2-dichlorobenzene, heptane, isooctane, methylcyclohexane, ethyl acetate, acetonitrile, anisole, tetrahydrofuran or butyronitrile. Preference is given to using tetrahydrofuran, anisole, toluene, xylene, chlorobenzene or acetonitrile. Particular preference is given to using toluene, chlorobenzene or anisole.

Bases used may be inorganic or organic bases. Examples here include: sodium hydroxide, potassium hydroxide, sodium carbonate, sodium hydrogencarbonate, potassium carbonate, potassium hydrogencarbonate, triethylamine, tributylamine, morpholine, piperidine, pyridine, 2-methyl-5-ethylpyridine. Preference is given to using sodium carbonate or potassium carbonate. Particular preference is given to using sodium carbonate. Particular preference is likewise given to using the mixture of sodium carbonate with sodium hydroxide.

The amount of base is guided by whether the hydrochlorides of the compounds of the general formulae (IV'), (V') and (VI') or the compounds of the general formulae (IV'), (V') and (VI') are being used. If the hydrochlorides of the compounds of the general formulae (IV'), (V') and (VI') are used, at least two molar equivalents of base will be used in order to convert the hydrochlorides in situ to the free compounds of the general formulae (IV'), (V') and (VI') and then to conduct the acylation reaction. If, by contrast, the free compounds of the general formulae (IV'), (V') and (VI') are used directly, at least one molar equivalent of base is used.

The acid chloride of the general formula (VII) can be used in any desired molar ratios based on the mixture of the compounds (IV'), (V') and (VI'). Typically between 0.9 and 2 molar equivalents of acid chloride are used, preferably between 0.95 and 1.3 molar equivalents.

The reaction temperature is between −10 and 120° C., preferably between 0 and 100° C.

The reaction can in principle also be conducted under reduced or elevated pressure.

The workup is effected by known methods in organic chemistry, for example by filtration or extraction.

Third step (3) of process (C) according to the invention: The mixture of the compounds of the general formulae (VIII'), (IX') and (X') is reacted in the presence of an inert diluent and an acid with an α,ω-diol of the general formula (XIV) to give the compound of the general formula (XVI).

Examples of useful diluents include: dichloromethane, toluene, ortho-, meta- or para-xylene, mesitylene, chlorobenzene, ortho-dichlorobenzene, acetonitrile, butyronitrile, tetrahydrofuran, 2-methyltetrahydrofuran, cyclopentyl methyl ether, methyl tert-butyl ether, tert-amyl methyl ether, 1,4-dioxane, anisole or mixtures of these solvents. Preference is given to anisole, toluene, ortho-, meta- or para-xylene, chlorobenzene, acetonitrile, butyronitrile, 2-methyltetrahydrofuran, cyclopentyl methyl ether, methyl tert-butyl ether, tert-amyl methyl ether or mixtures of these solvents. Particular preference is given to anisole, toluene, chlorobenzene.

The α,ω-diol of the general formula (XIV) is used in an amount of at least 0.5 mol based on 1 mol of the compounds of the general formulae (VIII'), (IX') and (X'). It is also possible to work in any excess of α,ω-diol of the general formula (XIV) and hence to simultaneously use it as solvent.

The third stage of process (C) according to the invention is conducted in the presence of a catalytic amount of an acid. Possible acids include, for example: hydrogen chloride, sulfuric acid, methanesulfonic acid, trifluoromethanesulfonic acid, para-toluenesulfonic acid or acidic ion exchange resins such as, for example, Amberlite. Preference is given to using sulfuric acid, hydrochloric acid or para-toluenesulfonic acid. Particular preference is given to using hydrochloric acid or para-toluenesulfonic acid.

The acid is used in amounts of 0.01 to 20 percent by weight, based on the compounds of the general formulae (VIII'), (IX') and (X'). Preference is given to 0.05 to 10 percent by weight.

The third stage of process (C) according to the invention is conducted at temperatures between 20 and 150° C.; preferably between 50 and 140° C.

To attain maximum conversion, it may be advantageous to remove the water of reaction formed, for example by distillation.

The compound of the general formula (XVI) is isolated by known customary methods in organic chemistry such as filtration, phase separation or extraction.

Fourth step (4) of process (C) according to the invention: The compound of the general formulae (XVI) is converted in the presence of an inert diluent and a strong base to the compound of the general formula (XI).

Examples of useful diluents include: toluene, ortho-, meta- or para-xylene, mesitylene, chlorobenzene, ortho-dichlorobenzene, acetonitrile, butyronitrile, tetrahydrofuran, 2-methyltetrahydrofuran, cyclopentyl methyl ether, methyl tert-butyl ether, tert-amyl methyl ether, 1,4-dioxane, N,N-dimethylformamide, N,N-dimethylacetamide, N-methylpyrrolidone, methanol, ethanol, 1-butanol, tert-butanol, anisole or mixtures of these solvents. Preference is given to N,N-dimethylformamide, N,N-dimethylacetamide, N-methylpyrrolidone, methanol, tert-butanol, anisole, chlorobenzene, ortho-dichlorobenzene or mixtures of these solvents. Particular preference is given to DMAc, NMP, xylene, toluene, chlorobenzene, anisole. Very particular preference is given to DMAc, toluene, chlorobenzene, anisole.

Bases used may, for example, be sodium methoxide, potassium methoxide, sodium ethoxide, potassium ethoxide, sodium propoxide, potassium propoxide, sodium tert-butoxide or potassium tert-butoxide. Preference is given to sodium hydroxide, sodium methoxide and potassium tert-butoxide. Particular preference is given to using sodium methoxide.

The bases are used in an amount of 0.9 to 4 molar equivalents, based on the compounds of the general formula (XVI). Preference is given to using 1 to 3.5 molar equivalents.

The temperature is between 20 and 170° C. Preference is given to working between 40 and 150° C.

After the pH of the reaction mixture has been adjusted to a value between 0 and 8, the compounds of the general formula (XI) are isolated by known customary methods in organic chemistry such as filtration, phase separation or extraction.

In a preferred embodiment of the invention, toluene is used as solvent in the second, third and fourth steps in process C.

In a preferred embodiment of the invention, toluene is used as solvent in the second and third steps and DMAc as solvent in the fourth step in process C.

In a preferred embodiment of the invention, chlorobenzene is used as solvent in the second, third and fourth steps in process C.

In a preferred embodiment of the invention, chlorobenzene is used as solvent in the second and third steps and DMAc as solvent in the fourth step in process C.

In a preferred embodiment of the invention, anisole is used as solvent in the second, third and fourth steps in process C.

In a preferred embodiment of the invention, chlorobenzene is used as solvent in the first, second, third and fourth steps in process C.

The present invention likewise provides novel compounds of the general formula (V')

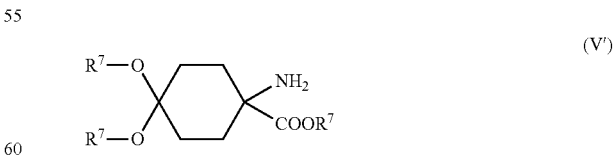

(V')

characterized in that the radical $R^7$ is optionally branched $C_2$- to $C_8$-alkyl.

Preferably, $R^7$ is ethyl, n-propyl, i-propyl, n-butyl or n-hexyl.

More preferably, $R^7$ is ethyl, n-propyl or n-butyl.

Exceptionally preferably, $R^7$ is n-propyl or n-butyl.

The present invention likewise provides novel compounds of the general formula (VI')

(VI')

in which
R$^7$ is optionally branched C$_3$- to C$_8$-alkyl.
Preferably, R$^7$ is n-propyl, i-propyl, n-butyl or n-hexyl.
More preferably, R$^7$ is n-propyl or n-butyl.
The present invention likewise provides novel compounds of the general formula (IX')

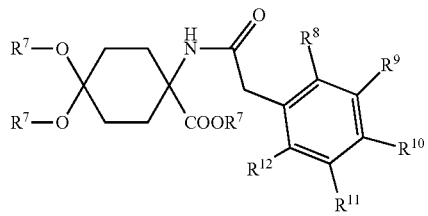

(IX')

in which
R$^7$ is optionally branched C$_2$- to C$_8$-alkyl
and
R$^8$, R$^9$, R$^{10}$, R$^{11}$ and R$^{12}$ are independently hydrogen, methyl, ethyl, optionally methyl-, ethyl-, methoxy-, ethoxy- or halogen-substituted phenyl, methoxy, ethoxy, fluorine, chlorine or bromine.
Most preferably,
R$^7$ is ethyl, n-propyl, i-propyl, n-butyl or n-hexyl,
R$^8$ is hydrogen, methyl, ethyl, methoxy, ethoxy, chlorine or bromine,
R$^9$ is hydrogen,
R$^{10}$ is hydrogen, methyl, chlorine or bromine,
R$^{11}$ is hydrogen
and
R$^{12}$ is hydrogen, methyl, ethyl, methoxy, ethoxy, chlorine or bromine.
Especially preferably,
R$^7$ is ethyl, n-propyl or n-butyl,
R$^8$ is methyl, ethyl, chlorine or bromine,
R$^9$ is hydrogen,
R$^{10}$ is hydrogen, chlorine or bromine,
R$^{11}$ is hydrogen
and
R$^{12}$ is methyl, ethyl, chlorine or bromine.
Exceptionally preferably,
R$^7$ is ethyl, n-propyl or n-butyl,
R$^8$ is methyl,
R$^9$ is hydrogen,
R$^{10}$ is chlorine,
R$^{11}$ is hydrogen
and
R$^{12}$ is methyl.
Very exceptionally preferably,
R$^7$ is n-propyl or n-butyl,
R$^8$ is methyl,
R$^9$ is hydrogen,
R$^{10}$ is chlorine,
R$^{11}$ is hydrogen
and
R$^{12}$ is methyl.
The present invention likewise provides novel compounds of the general formula (X')

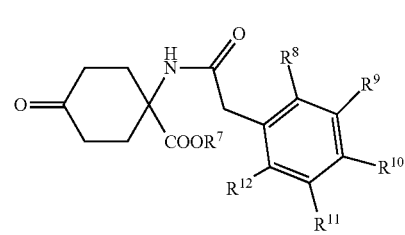

(X')

in which
R$^7$ is optionally branched C$_2$- to C$_8$-alkyl
and
R$^8$, R$^9$, R$^{10}$, R$^{11}$ and R$^{12}$ are independently hydrogen, methyl, ethyl, optionally methyl-, ethyl-, methoxy-, ethoxy- or halogen-substituted phenyl, methoxy, ethoxy, fluorine, chlorine or bromine.
Most preferably,
R$^7$ is ethyl, n-propyl, i-propyl, n-butyl or n-hexyl,
R$^8$ is hydrogen, methyl, ethyl, methoxy, ethoxy, chlorine or bromine,
R$^9$ is hydrogen,
R$^{10}$ is hydrogen, methyl, chlorine or bromine,
R$^{11}$ is hydrogen
and
R$^{12}$ is hydrogen, methyl, ethyl, methoxy, ethoxy, chlorine or bromine.
Especially preferably,
R$^7$ is ethyl, n-propyl or n-butyl,
R$^8$ is methyl, ethyl, chlorine or bromine,
R$^9$ is hydrogen,
R$^{10}$ is hydrogen, chlorine or bromine,
R$^{11}$ is hydrogen
and
R$^{12}$ is methyl, ethyl, chlorine or bromine.
Exceptionally preferably,
R$^7$ is ethyl, n-propyl or n-butyl,
R$^8$ is methyl,
R$^9$ is hydrogen,
R$^{10}$ is chlorine,
R$^{11}$ is hydrogen
and
R$^{12}$ is methyl.
Very exceptionally preferably,
R$^7$ is n-propyl or n-butyl,
R$^8$ is methyl,
R$^9$ is hydrogen,
R$^{10}$ is chlorine,
R$^{11}$ is hydrogen
and
R$^{12}$ is methyl.

The present invention likewise provides novel compounds of the general formula (XII')

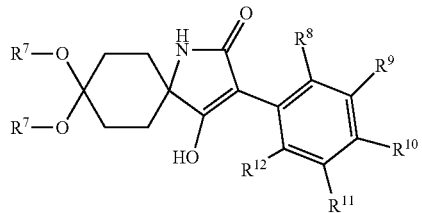

(XII')

in which
R$^7$ is optionally branched C$_2$- to C$_8$-alkyl
and
R$^8$, R$^9$, R$^{10}$, R$^{11}$ and R$^{12}$ are independently hydrogen, methyl, ethyl, optionally methyl-, ethyl-, methoxy-, ethoxy- or halogen-substituted phenyl, methoxy, ethoxy, fluorine, chlorine or bromine.
Most preferably,
R$^7$ is ethyl, n-propyl, i-propyl, n-butyl or n-hexyl,
R$^8$ is hydrogen, methyl, ethyl, methoxy, ethoxy, chlorine or bromine,
R$^9$ is hydrogen,
R$^{10}$ is hydrogen, methyl, chlorine or bromine,
R$^{11}$ is hydrogen
and
R$^{12}$ is hydrogen, methyl, ethyl, methoxy, ethoxy, chlorine or bromine.
Especially preferably,
R$^7$ is ethyl, n-propyl or n-butyl,
R$^8$ is methyl, ethyl, chlorine or bromine,
R$^9$ is hydrogen,
R$^{10}$ is hydrogen, chlorine or bromine,
R$^{11}$ is hydrogen
and
R$^{12}$ is methyl, ethyl, chlorine or bromine.
Exceptionally preferably,
R$^7$ is ethyl, n-propyl or n-butyl,
R$^8$ is methyl,
R$^9$ is hydrogen,
R$^{10}$ is chlorine,
R$^{11}$ is hydrogen
and
R$^{12}$ is methyl.
Very exceptionally preferably,
R$^7$ is n-propyl or n-butyl,
R$^8$ is methyl,
R$^9$ is hydrogen,
R$^{10}$ is chlorine,
R$^{11}$ is hydrogen
and
R$^{12}$ is methyl.
The above-listed general radical definitions and elucidations or those listed in preferred ranges may be combined arbitrarily with one another, in other words including combinations between the respective ranges and preferred ranges. They apply both to the end products and, correspondingly, to the precursors and intermediates.

The present invention is illustrated in detail by the examples which follow without being restricted thereby.

EXAMPLES

Example 1

Methyl 8-amino-1,4-dioxaspiro[4.5]decane-8-carboxylate, methyl 1-amino-4,4-dimethoxycyclohexanecarboxylate and methyl 1-amino-4-oxocyclohexanecarboxylate

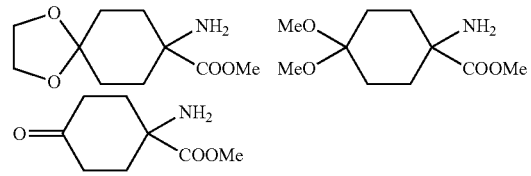

29.1 g [0.145 mol] of 8-amino-1,4-dioxaspiro[4.5]decane-8-carboxylic acid form an initial charge in 160 g of methanol. At 0-5° C., while cooling, 34.4 g [0.289 mol] of thionyl chloride are metered in. The mixture is left to warm up to 20° C., and stirred at 20° C. for 16 hours and then under reflux (64° C.) for another 4 hours. Methanol and thionyl chloride are distilled off under reduced pressure. The residue is adjusted to pH 8 with sodium hydroxide solution (32%) and extracted twice with 100 ml each time of methyl tert-butyl ether (MTBE). The combined organic phases are dried over sodium sulfate and concentrated under reduced pressure. 19.5 g of residue are obtained, which, by $^1$H and $^{13}$C NMR analyses, consists of the three title compounds.

Composition by quantitative $^1$H NMR: 61% methyl 8-amino-1,4-dioxaspiro[4.5]decane-8-carboxylate; 9% methyl 1-amino-4,4-dimethoxycyclohexanecarboxylate; 21% methyl 1-amino-4-oxocyclohexanecarboxylate.

Methyl 8-amino-1,4-dioxaspiro[4.5]decane-8-carboxylate: $^{13}$C-NMR (150 MHz, d-DMSO): δ=30.2 (CH$_2$), 32.5 (CH$_2$), 51.8 (Me-OCO), 55.9 (C(NH$_2$)COOMe), 63.7 (O—CH$_2$—C), 63.8 (O—CH$_2$—C), 107.8 (C—OCCO—), 177.6 (C(=O)OMe) ppm.

Methyl 1-amino-4,4-dimethoxycyclohexanecarboxylate: $^{13}$C-NMR (150 MHz, d-DMSO): δ=27.7 (CH$_2$), 31.5 (CH$_2$), 47.0 (MeO—C(OMe)), 47.1 (MeO—C(OMe)), 51.8 (Me-OCO), 56.2 (C(NH$_2$)COOMe), 99.2 (C(OMe)$_2$), 177.6 (C(=O)OMe) ppm.

Methyl 1-amino-4-oxocyclohexanecarboxylate: $^{13}$C-NMR (150 MHz, d-DMSO): δ=34.1 (CH$_2$), 36.6 (CH$_2$), 52.0 (Me-OCO), 55.7 (C(NH$_2$)COOMe), 177.1 (C(=O)OMe), 210.1 (C—C(=O)—C) ppm.

Example 2

Ethyl 8-amino-1,4-dioxaspiro[4.5]decane-8-carboxylate and ethyl 1-amino-4-oxocyclohexanecarboxylate

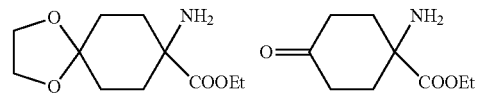

The procedure is as in Example 1, except that ethanol is used rather than methanol. 29 g of mixture are obtained, which, by $^1$H and $^{13}$C NMR analyses, consists of the two title compounds.

Composition by quantitative $^1$H NMR: 83.6% ethyl 8-amino-1,4-dioxaspiro[4.5]decane-8-carboxylate; 16.7% ethyl 1-amino-4-oxocyclohexanecarboxylate.

Ethyl 8-amino-1,4-dioxaspiro[4.5]decane-8-carboxylate: $^{13}$C-NMR (150 MHz, d-DMSO): δ=14.2 (CH$_3$—CH$_2$O (CO)), 30.3 (CH$_2$), 32.5 (CH$_2$), 55.9 (C(NH$_2$)COOMe), 60.3 (CH$_3$—CH$_2$O(CO)), 63.8 (O—CH$_2$—C), 107.8 (C—OCCO—), 177.1 (C(=O)OMe) ppm.

Ethyl 1-amino-4-oxocyclohexanecarboxylate: $^{13}$C-NMR (150 MHz, d-DMSO): δ=14.2 (CH$_3$—CH$_2$O(CO)), 34.2 (CH$_2$), 36.6 (CH$_2$), 55.6 (C(NH$_2$)COOMe), 60.5 (CH$_3$—CH$_2$O(CO)), 176.6 (C(=O)OMe), 210.2 ((C—C(=O)—C) ppm.

Example 3 n-Propyl 8-amino-1,4-dioxaspiro[4.5]decane-8-carboxylate

The procedure is as in Example 1, except that 1-propanol is used rather than methanol. This gives 29.5 g of the title compound.

Purity by quantitative $^1$H NMR: 90%.

n-Propyl 8-amino-1,4-dioxaspiro[4.5]decane-8-carboxylate: $^{13}$C-NMR (150 MHz, d-DMSO): δ=10.4 (CH$_3$—CH$_2$CH$_2$O(CO)), 21.7 (CH$_3$—CH$_2$CH$_2$O(CO)), 30.3 (CH$_2$), 32.5 (CH$_2$), 56.0 (C(NH$_2$)COOMe), 63.8 (O—CH$_2$—C), 65.7 (CH$_3$CH$_2$—CH$_2$O(CO)), 107.8 (C—OCCO—), 177.1 (C(=O)OMe) ppm.

Example 4 n-Propyl 8-amino-1,4-dioxaspiro[4.5]decane-8-carboxylate, n-propyl 1-amino-4,4-dipropoxycyclohexanecarboxylate and n-propyl 1-amino-4-oxocyclohexanecarboxylate

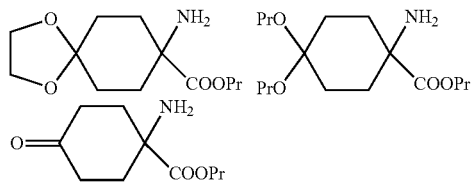

99 g [0.492 mol] of 8-amino-1,4-dioxaspiro[4.5]decane-8-carboxylic acid form an initial charge in 200 g of 1-propanol. At 0-5° C., while cooling, 76.1 g [0.64 mol] of thionyl chloride are metered in within one hour. The mixture is left to warm up to 20° C., and stirred at 20° C. for 16 hours and then under reflux for another 6 hours. Propanol and thionyl chloride are distilled off under reduced pressure. The residue is adjusted to pH 8 with aqueous sodium carbonate solution and extracted twice with 150 ml each time of methyl tert-butyl ether (MTBE). The combined organic phases are washed with 50 ml of water, dried over sodium sulfate and concentrated under reduced pressure. 100 g of residue are obtained, which, by $^1$H and $^{13}$C NMR analyses, consists of the three title compounds.

Composition by quantitative $^1$H NMR: 69% n-propyl 8-amino-1,4-dioxaspiro[4.5]decane-8-carboxylate; 16% n-propyl 1-amino-4,4-dipropoxycyclohexanecarboxylate; 10% n-propyl 1-amino-4-oxocyclohexanecarboxylate.

n-Propyl 8-amino-1,4-dioxaspiro[4.5]decane-8-carboxylate: $^{13}$C-NMR (150 MHz, d6-DMSO): δ=10.4 (CH$_3$—CH$_2$CH$_2$O(CO)), 21.7 (CH$_3$—CH$_2$CH$_2$O(CO)), 30.3 (CH$_2$), 32.5 (CH$_2$), 56.0 (C(NH$_2$)COOMe), 63.8 (O—CH$_2$—C), 65.7 (CH$_3$CH$_2$—CH$_2$O(CO)), 107.8 (C—OCCO—), 177.1 (C(=O)OMe) ppm.

n-Propyl 1-amino-4,4-dipropoxycyclohexanecarboxylate: $^{13}$C-NMR (150 MHz, d6-DMSO): δ=10.5 (CH$_3$—CH$_2$CH$_2$O(CO)), 11.0/11.1 (C(OCH$_2$CH$_2$CH$_3$)$_2$), 21.7 (CH$_3$—CH$_2$CH$_2$O(CO)), 23.0 (2×CH$_2$), 30.3 (2×CH$_2$), 32.6 (2×CH$_2$), 56.0 (C(NH$_2$)COOPr), 60.7/60.8 (C(OCH$_2$CH$_2$CH$_3$)$_2$), 65.7 (CH$_3$CH$_2$—CH$_2$O(CO)), 98.9 (C(OCH$_2$CH$_2$CH$_3$)$_2$), 177.2 (C—CO—OPr) ppm.

n-Propyl 1-amino-4-oxo-cyclohexanecarboxylate: $^{13}$C-NMR (150 MHz, d6-DMSO): δ=10.4 (CH$_3$—CH$_2$CH$_2$O(CO)), 21.5 (CH$_3$—CH$_2$CH$_2$O(CO)), 29.6 (2×CH$_2$), 35.8 (2×CH$_2$), 57.3 (C(NH$_2$)COOPr), 67.9 (CH$_3$CH$_2$—CH$_2$O(CO)), 170.9 (C—CO—OPr), 207.8 (C—(C=O)—C) ppm.

Example 5 n-Butyl 8-amino-1,4-dioxaspiro[4.5]decane-8-carboxylate and n-butyl 1-amino-4,4-dibutoxycyclohexanecarboxylate

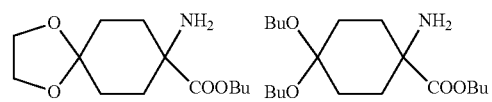

The procedure is as in Example 1, except that 1-butanol is used rather than methanol. 39 g of mixture are obtained, which, by $^1$H and $^{13}$C NMR analyses, consists of the two title compounds.

Composition by quantitative $^1$H NMR: 69% n-butyl 8-amino-1,4-dioxaspiro[4.5]decane-8-carboxylate and 23% n-butyl 1-amino-4,4-dibutoxycyclohexanecarboxylate.

n-Butyl 8-amino-1,4-dioxaspiro[4.5]decane-8-carboxylate: $^{13}$C-NMR (150 MHz, d6-DMSO): δ=13.7 (CH$_3$—CH$_2$CH$_2$CH$_2$O(CO)), 18.8 (CH$_3$—CH$_2$CH$_2$CH$_2$O(CO)), 30.4 (CH$_3$—CH$_2$CH$_2$CH$_2$O(CO)), 30.4 (CH$_2$), 32.6 (CH$_2$), 56.0 (C(NH$_2$)COOMe), 63.7 (O—CH$_2$—C), 63.9 (CH$_3$CH$_2$CH$_2$—CH$_2$O(CO)), 107.8 (C—OCCO—), 177.1 (C(=O)OMe) ppm.

n-Butyl 1-amino-4,4-dibutoxycyclohexanecarboxylate: $^{13}$C-NMR (150 MHz, d6-DMSO): δ=13.7 (CH$_3$—CH$_2$CH$_2$CH$_2$O(CO)), 14.0 (CH$_3$CH$_2$CH$_2$CH$_2$O—C(OBu), 18.8 (CH$_3$—CH$_2$CH$_2$CH$_2$O(CO)), 19.3 (CH$_3$CH$_2$CH$_2$CH$_2$O—C(OBu), 28.7 (CH$_2$), 30.4 (CH$_3$—CH$_2$CH$_2$CH$_2$O(CO)), 31.6 (CH$_2$), 31.9 (CH$_3$CH$_2$CH$_2$—CH$_2$O—C(OBu), 56.2 (C(NH$_2$)COOBu), 58.8 (CH$_3$CH$_2$CH$_2$CH$_2$O—C(OBu), 63.8 (CH$_3$—CH$_2$CH$_2$CH$_2$O(CO)), 98.9 (C(OBu)$_2$), 177.2 (C(=O)OBu) ppm.

Example 6 n-Propyl 8-[2-(4-chloro-2,6-dimethylphenyl)acetamido]-1,4-dioxaspiro[4.5]decane-8-carboxylate

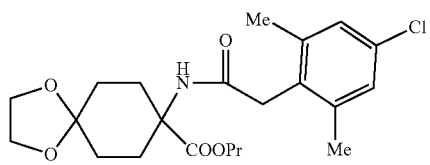

27 g [0.111 mol] of n-propyl 8-amino-1,4-dioxaspiro[4.5]decane-8-carboxylate (compound from Example 3) form an initial charge in 70 g of 20% aqueous sodium hydrogencarbonate solution. At about 5° C., a solution of 24.1 g [0.111 mol] of (4-chloro-2,6-dimethylphenyl)acetyl chloride in 20.3 g of toluene is metered in within about 2 hours. During this metered addition, 35 g of water and 50 g of toluene are added to the reaction mixture. After the metered addition has ended, stirring is continued at 20° C. for another 1 hour, and the solids are filtered off with suction, washed with water and dried. This gives 29.5 g of the title compound.

Purity by quantitative $^1$H NMR: 92%.

$^{13}$C-NMR (150 MHz, d6-DMSO): δ=10.4 (CH$_3$—CH$_2$CH$_2$O(CO)), 19.9 (CH$_3$—Ar), 21.7 (CH$_3$—CH$_2$CH$_2$O(CO)), 29.9 (CH$_2$), 30.2 (CH$_2$), 35.2 (N—CO—CH$_2$—Ar), 57.5 (C(NHCO)COOPr), 63.8 (O-CH$_2$CH$_2$O), 65.9 (CH$_3$CH$_2$—CH$_2$O(CO)), 107.3 (C(OCH$_2$CH$_2$)), 127.1 (C$_{Ar}$—H), 130.4 (C$_{Ar}$—Cl), 133.0 (COCH$_2$—C$_{Ar}$), 139.6 (C$_{Ar}$-Me), 169.6 (N—CO—CH$_2$), 173.7 (C—CO—OPr) ppm.

Reprecipitation:

n-Propyl 1-[2-(4-chloro-2,6-dimethylphenyl)acetamido]-4-oxocyclohexanecarboxylate

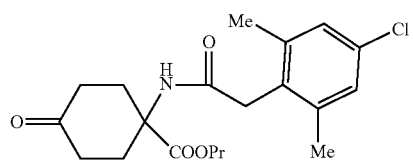

n-Propyl 1-[2-(4-chloro-2,6-dimethylphenyl)acetamido]-4-oxocyclohexanecarboxylate: $^{13}$C-NMR (150 MHz, d6-DMSO): δ=10.4 (CH$_3$—CH$_2$CH$_2$O(CO)), 19.9 (CH$_3$—Ar), 21.7 (CH$_3$—CH$_2$CH$_2$O(CO)), 31.5 (CH$_2$), 35.2 (N—CO—CH$_2$—Ar), 36.4 (CH$_2$), 57.2 (C(NHCO)COOPr), 66.2 (CH$_3$CH$_2$—CH$_2$O(CO)), 127.0 (C$_{Ar}$—H), 130.4 (C$_{Ar}$—Cl), 132.9 (COCH$_2$—C$_{Ar}$), 139.7 (C$_{Ar}$-Me), 170.0 (N—CO—CH$_2$), 173.1 (C—CO—OPr), 209.1 (C—CO—C) ppm.

n-Propyl 1-[[2-(4-chloro-2,6-dimethylphenyl)acetyl]amino]-4,4-dipropoxycyclohexanecarboxylate

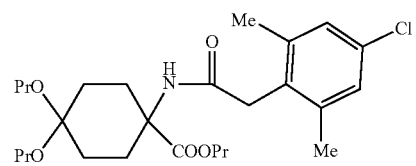

$^{13}$C-NMR (150 MHz, d6-DMSO): δ=10.4 (CH$_3$—CH$_2$CH$_2$O(CO)), 11.0 (2×C(OCH$_2$CH$_2$CH$_3$)$_2$), 20.1 (2×Aryl-CH$_3$), 21.6 (CH$_3$—CH$_2$CH$_2$O(CO)), 22.9/23.0 (2×CH$_2$), 28.6 (2×CH$_2$), 28.9 (2×CH$_2$), 35.2 (Aryl-CH$_2$—(CO)N), 57.8 (C(NH$_2$)COOPr), 60.8/60.9 (C(OCH$_2$CH$_2$CH$_3$)$_2$), 65.8 (CH$_3$CH$_2$—CH$_2$O(CO)), 98.5 (C(OCH$_2$CH$_2$CH$_3$)$_2$), 126.6 (2×C$_{Ar}$—H), 128.8 (C$_{Ar}$—Cl), 136.3 (COCH$_2$—C$_{Ar}$), 138.9 (2×C$_{Ar}$-Me), 169.4 (N—CO—CH$_2$), 173.7 (C—CO—OPr) ppm.

Example 7

Methyl 8-amino-1,4-dioxaspiro[4.5]decane-8-carboxylate and methyl 1-amino-4,4-dimethoxycyclohexanecarboxylate

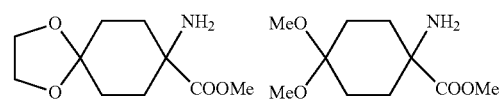 [SMILES: COC(=O)C1(N)CCC2(CC1)OCCO2 ; COC(=O)C1(N)CCC(OC)(OC)CC1]

2748 g [11.56 mol] of 8-amino-1,4-dioxaspiro[4.5]decane-8-carboxylic acid hydrochloride form an initial charge in 50 l of methanol and then, at 5-10° C., 2050 g [17.23 mol] of thionyl chloride are metered in within 1 hour. The mixture is stirred at 40-45° C. for 48 hours, then cooled down to 5° C., the mixture is filtered and the solids are washed with 3 l of methanol. The filtrate is concentrated under reduced pressure. The residue obtained is stirred in a solution of 1900 g of potassium carbonate in 8 l of water and extracted five times with 8 l each time of methylene chloride. The combined organic phases are dried over sodium sulfate and concentrated under reduced pressure. This gives 2240 g of oil, which, by GC-MS analysis, contains 65.4% methyl 8-amino-1,4-dioxaspiro[4.5]decane-8-carboxylate and 31.1% methyl 1-amino-4,4-dimethoxycyclohexanecarboxylate.

Example 8

Methyl 8-[2-(4-chloro-2,6-dimethylphenyl)acetamido]-1,4-dioxaspiro[4.5]decane-8-carboxylate, methyl 1-[2-(4-chloro-2,6-dimethylphenyl)acetamido]-4,4-dimethoxycyclohexanecarboxylate and methyl 1-[2-(4-chloro-2,6-dimethylphenyl)acetamido]-4-oxocyclohexanecarboxylate

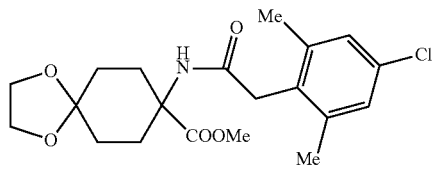

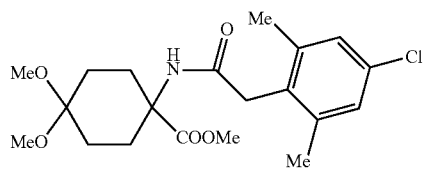

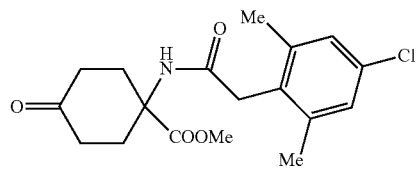

100 g of a mixture of 67.5% methyl 8-amino-1,4-dioxaspiro[4.5]decane-8-carboxylate [0.313 mol], 30.1% methyl 1-amino-4,4-dimethoxycyclohexanecarboxylate [0.138 mol] and 0.5% methyl 1-amino-4-oxocyclohexanecarboxylate [0.003 mol] are dissolved in 1.44 l of acetonitrile. While stirring, 121 g of potassium carbonate are added and then about 90 ml of water-moist acetonitrile are distilled off for azeotropic drying. Thereafter, the mixture is cooled to 5° C. and a solution of 95.5 g [0.44 mol] of (4-chloro-2,6-dimethylphenyl)acetyl chloride is added dropwise within 2 hours. The mixture is then stirred at 5° C. for another 2 hours and at 20° C. for 16 hours, then the reaction mixture is stirred into 6.6 l of water and filtered, and the solids are washed with 0.7 l of water and dried. The result is 165 g of white solid which, by GC-MS analysis, consists to an extent of 69.2% of methyl 8-[2-(4-chloro-2,6-dimethylphenyl)acetamido]-1,4-dioxaspiro[4.5]decane-8-carboxylate, 20.1% methyl 1-[2-(4-chloro-2,6-dimethylphenyl)acetamido]-4,4-dimethoxycyclohexanecarboxylate and 7.8% methyl 1-[2-(4-chloro-2,6-dimethylphenyl)acetamido]-4-oxocyclohexanecarboxylate.

Example 9

Methyl 8-[2-(4-chloro-2,6-dimethylphenyl)acetamido]-1,4-dioxaspiro[4.5]decane-8-carboxylate, methyl 1-[2-(4-chloro-2,6-dimethylphenyl)acetamido]-4,4-dimethoxycyclohexanecarboxylate and methyl 1-[2-(4-chloro-2,6-dimethylphenyl)acetamido]-4-oxocyclohexanecarboxylate

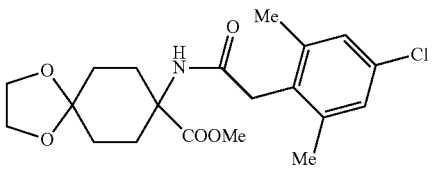

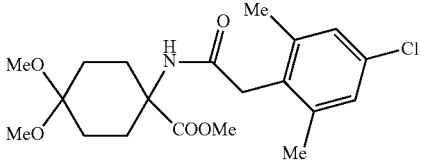

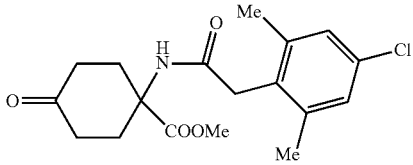

To an initial charge of 5 g of 8-[2-(4-chloro-2,6-dimethylphenyl)acetamido]-1,4-dioxaspiro[4.5]decane-8-carboxylic acid of purity 84.6% (4.23 g, 11.1 mmol) in 50 ml of methanol is added 0.11 g conc. sulfuric acid, and the mixture is heated under reflux for 16 hours. Subsequently, the reaction mixture is concentrated under reduced pressure. This gives 5.5 g of residue which, by GC-MS analysis, consists to an extent of 57.6% of methyl 8-[2-(4-chloro-2,6-dimethylphenyl)acetamido]-1,4-dioxaspiro[4.5]decane-8-carboxylate and 35.2% methyl 1-[2-(4-chloro-2,6-dimethylphenyl)acetamido]-4,4-dimethoxycyclohexanecarboxylate.

Example 10

11-(4-Chloro-2,6-dimethylphenyl)-12-hydroxy-1,4-dioxa-9-azadispiro[4.2.48.25]tetradec-11-en-10-one, 3-(4-chloro-2,6-dimethylphenyl)-4-hydroxy-8,8-dimethoxy-1-azaspiro[4.5]dec-3-en-2-one and 3-(4-chloro-2,6-dimethylphenyl)-4-hydroxy-1-azaspiro[4.5]dec-3-ene-2,8-dione

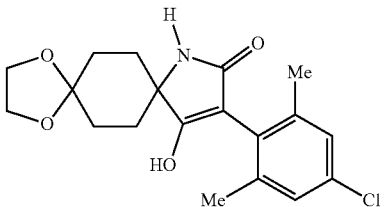 [SMILES: Cc1cc(Cl)cc(C)c1C1=C(O)C2(CCC3(CC2)OCCO3)NC1=O]

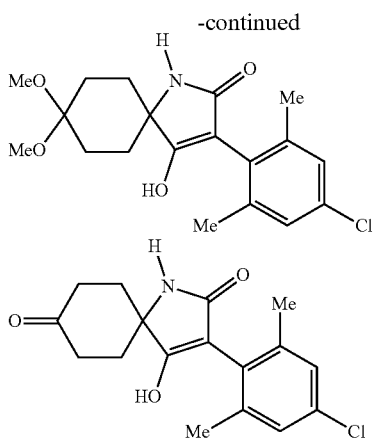

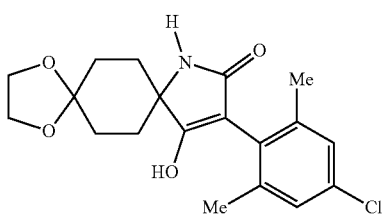

5491 g [48.934 mol] of KOtBu are dissolved in 31 l of dimethylformamide (DMF), and then 6550 g of a mixture of 68.3% methyl 8-[2-(4-chloro-2,6-dimethylphenyl)acetamido]-1,4-dioxaspiro[4.5]decane-8-carboxylate, 16.8% methyl 1-[2-(4-chloro-2,6-dimethylphenyl)acetamido]-4,4-dimethoxycyclohexanecarboxylate and 12.1% methyl 1-[2-(4-chloro-2,6-dimethylphenyl)acetamido]-4-oxocyclohexanecarboxylate are added in portions within 2 hours, in the course of which the reaction mixture warms up to 40° C. The mixture is stirred at 40° C. for another 3 hours and at room temperature overnight, 26 l of DMF are distilled off under reduced pressure, 75 l of ice-water are added to the residue, 4 l of glacial acetic acid are added thereto and the mixture is stirred at 15° C. overnight. The precipitated solids are filtered off with suction, washed three times with 5 l each time of water and dried. The result is 5720 g of the following composition by HPLC analysis:

71.8% 11-(4-chloro-2,6-dimethylphenyl)-12-hydroxy-1,4-dioxa-9-azadispiro[4.2.48.25]tetradec-11-en-10-one;
13.4% 3-(4-chloro-2,6-dimethylphenyl)-4-hydroxy-8,8-dimethoxy-1-azaspiro[4.5]dec-3-en-2-one and 8.3% 3-(4-chloro-2,6-dimethylphenyl)-4-hydroxy-1-azaspiro[4.5]dec-3-ene-2,8-dione.

Example 11

11-(4-Chloro-2,6-dimethylphenyl)-12-hydroxy-1,4-dioxa-9-azadispiro[4.2.48.25]tetradec-11-en-10-one

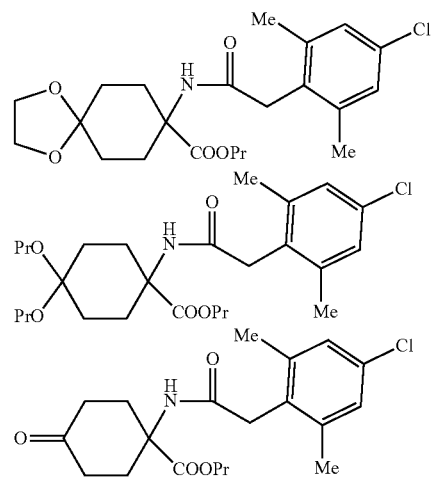

The 5720 g of product mixture from Example 10 are suspended in 27 l of ethylene glycol, and 95 g of para-toluenesulfonic acid are added. The mixture is heated to about 130° C. (bath temperature 155° C.) for two hours with stirring. Subsequently, at the same bath temperature, 4 l of acetonitrile are metered in, which results in a drop in the internal temperature to about 111° C. The mixture is stirred at the same bath temperature for three hours, and the acetonitrile is distilled off first at standard pressure, later on at a pressure reduced down to about 200 mbar, until the internal temperature is about 130° C. again. The mixture is stirred at 130° C. overnight, then cooled down to room temperature, and the solids are filtered off with suction, stirred in 30 l of water for one hour, filtered off with suction again, washed with 10 l of water and dried. This gives 5080 g of a pale beige solid which, by HPLC analysis, consists to an extent of 99.3% of the title compound.

Example 12

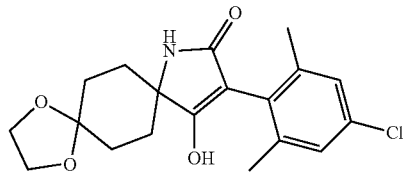 [SMILES: Cc1cc(Cl)cc(C)c1C1=C(O)C2(CCC3(CC2)OCCO3)NC1=O]

An initial charge of 60 g [0.296 mol] of 8-amino-1,4-dioxaspiro[4.5]decane-8-carboxylic acid (99%) in 154 g of 1-propanol is heated to 80-85° C., and 24.8 g of thionyl chloride are metered in at 0.5 ml/min. After the metered addition has ended, the mixture is stirred at 90° C. for a further 3 h, then cooled down to 40-45° C. At about 30 mbar, 89 g of distillate are removed, then the vacuum is broken and the mixture is cooled to 5-10° C. A mixture of 9.3 g of NaOH and 61.9 g of $Na_2CO_3$ dissolved in 300 g of water is then metered in at such a rate that the internal temperature always remains below 10° C. Then 128.6 g of 2-(4-chloro-2,6-dimethylphenyl)acetyl chloride in THF (42.2% solution) are metered into the reaction mixture at 2.5 ml/min. 200 g of THF are added and the mixture is adjusted to pH 7-8 with dilute HCl. The organic phase is removed and concentrated on a rotary evaporator. This gives 125 g of a mixture of n-propyl 8-[[2-(4-chloro-2,6-dimethylphenyl)acetyl]amino]-1,4-dioxaspiro[4.5]decane-8-carboxylate (65%)/n-propyl 1-[[2-(4-chloro-2,6-dimethylphenyl)acetyl]amino]-4,4-dipropoxycyclohexanecarboxylate (8%)/n-propyl 1-[[2-(4-chloro-2,6-dimethylphenyl)acetyl]amino]-4-oxocyclohexanecarboxylate (13%). Yield: 86%.

Example 13

20 g [0.041 mol] of the isolated crude product from Example 12 are stirred in 60 g of xylene, 3.9 g of ethanediol and 0.3 g of para-toluenesulfonic acid at 130° C. for 4 h, a further 0.9 g of para-toluenesulfonic acid and 3.9 g of ethanediol are added and the mixture is refluxed for a further 8 h. Then the xylene is distilled off on a rotary evaporator and the residue is taken up in 80 g of DMAc. The DMAc is incipiently distilled and, after the removal of 25 g of distillate, 8 g of sodium methoxide (30% solution in methanol) are added at internal temperature 110° C. Incipient distillation is repeated at 250 mbar and internal temperature of about 100-110° C., then the mixture is cooled down to 80° C. and 50 g of water are added, followed by 10 g of acetic acid. After cooling to room temperature, the suspension is filtered with suction and washed with 30 g of water. This gives 9.5 g of 2-(4-chloro-2,6-dimethylphenyl)-1-hydroxy-9,12-dioxa-4-azadispiro[4.2.48.25]tetradec-1-en-3-one in 64% yield and 97% purity.

Example 14

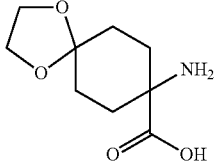 [SMILES: NC1(C(=O)O)CCC2(CC1)OCCO2]

550 g of sodium 8-amino-1,4-dioxaspiro[4.5]decane-8-carboxylate (~78% purity) are initially charged in 724 g of water at room temperature. 20% HCl is added gradually to the mixture until the pH is 5-6. The suspension is filtered off with suction, and the filtercake is washed with 212.6 g of water and then dried. Yield: 356.7 g (92%) of 8-amino-1,4-dioxaspiro[4.5]decane-8-carboxylic acid, purity 94% by quant. NMR $^1$H-NMR (600 MHz, d-D$_2$O+1 drop NaOD): δ=1.55-1.60 (m, 2H), 1.69-1.73 (m, 2H), 1.77-1.82 (m, 2H), 2.00-2.04 (m, 2H), 4.021 (s, 4H) ppm.

Example 15

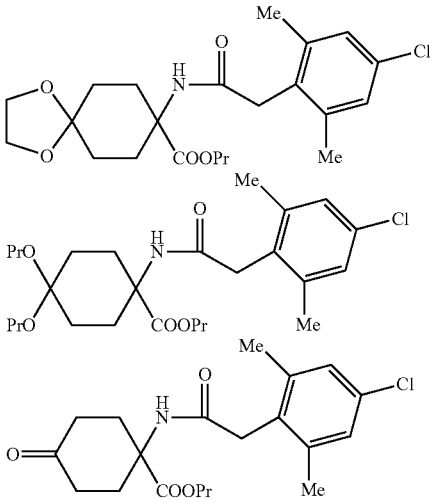

An initial charge of 370.7 g [0.296 mol] of 8-amino-1,4-dioxaspiro[4.5]decane-8-carboxylic acid (96.7%) in 1178 g of 1-propanol is heated to 80-85° C., and 233 g of thionyl chloride are metered in within 2 h. After the metered addition has ended, the mixture is stirred at 90° C. for a further 3 h and the ~22-25% (w/w) solution is used for further reactions.

Example 16

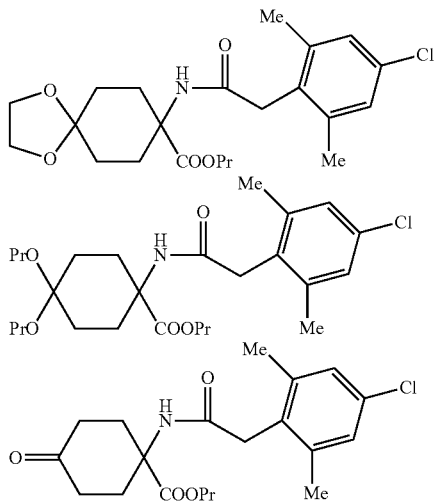

235.3 g of a solution that has been prepared analogously to Example 15 is incipiently distilled at internal temperature 25-30° C. and 25 mbar. After removal of 128.9 g of distillate, the vacuum is broken with nitrogen and the mixture is brought to standard pressure. After the mixture has been cooled to 0-5° C., 43.8 g of Na$_2$CO$_3$ dissolved in 400 g of water are metered in sufficiently slowly that the temperature always remains below 5° C. After the metered addition has ended, 121.9 g of 2-(4-chloro-2,6-dimethylphenyl)acetyl chloride (39.5% in toluene, 0.85 eq) are added within one hour at such a rate that the internal temperature does not exceed 5° C. The mixture is stirred at 0-5° C. for a further 1 h and then heated to 73° C. The organic phase is removed and concentrated on a rotary evaporator. This gives 98.8 g of a pale yellow solid composed of propyl 8-[[2-(4-chloro-2,6-dimethylphenyl)acetyl]amino]-1,4-dioxaspiro[4.5]decane-8-carboxylate (84%)/propyl 1-[[2-(4-chloro-2,6-dimethylphenyl)acetyl]amino]-4,4-dipropoxycyclohexanecarboxylate (7%)/propyl 1-[[2-(4-chloro-2,6-dimethylphenyl)acetyl]amino]-4-oxocyclohexanecarboxylate (7%). The yield is quantitative.

Example 17

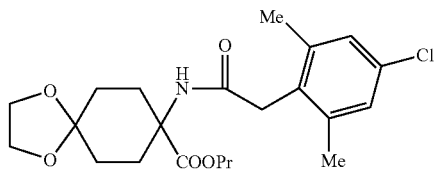

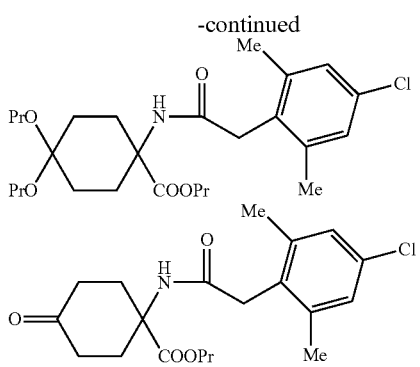

232.4 g of a solution that has been prepared analogously to Example 15 is incipiently distilled at internal temperature 25-30° C. and 25 mbar. After removal of 126.8 g of distillate, the vacuum is broken with nitrogen and the mixture is brought to standard pressure. After the mixture has been cooled to 0-5° C., 43.7 g of Na₂CO₃ dissolved in 400 g of water are metered in sufficiently slowly that the temperature always remains below 5° C. After the metered addition has ended, 133.6 g of 2-(4-chloro-2,6-dimethylphenyl)acetyl chloride (39.5% in toluene) are then added within one hour at such a rate that the internal temperature does not exceed 5° C. The mixture is stirred at 0-5° C. for a further 3 h and then heated to 75° C. The organic phase is removed and concentrated on a rotary evaporator. This gives 103.5 g of a pale yellow solid composed of propyl 8-[[2-(4-chloro-2,6-dimethylphenyl)acetyl]amino]-1,4-dioxaspiro[4.5]decane-8-carboxylate (79%)/propyl 1-[[2-(4-chloro-2,6-dimethylphenyl)acetyl]amino]-4,4-dipropoxycyclohexanecarboxylate (8%)/propyl 1-[[2-(4-chloro-2,6-dimethylphenyl)acetyl]amino]-4-oxocyclohexanecarboxylate (7%). The yield is 97%.

Example 18

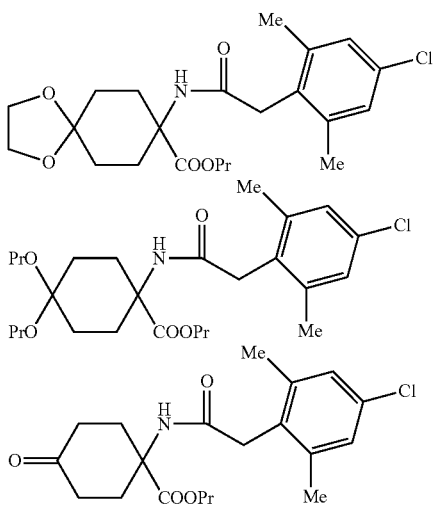

233.2 g of a solution that has been prepared analogously to Example 15 is incipiently distilled at internal temperature 25-30° C. and 25 mbar. After removal of 130.6 g of distillate, the vacuum is broken with nitrogen and the mixture is brought to standard pressure. After the mixture has been cooled to 0-10° C., 43.8 g of Na₂CO₃ dissolved in 381.7 g of water and 32.6 g of 32% sodium hydroxide solution are metered in sufficiently slowly that the temperature always remains below 5° C. After the metered addition has ended, 121.9 g of 2-(4-chloro-2,6-dimethylphenyl)acetyl chloride (39.5% in toluene) are then added within one hour at such a rate that the internal temperature does not exceed 5° C. The mixture is stirred at 0-5° C. for a further 30 min and then heated to 72° C. The organic phase is removed and concentrated on a rotary evaporator. This gives 97.1 g of a pale yellow solid composed of propyl 8-[[2-(4-chloro-2,6-dimethylphenyl)acetyl]amino]-1,4-dioxaspiro[4.5]decane-8-carboxylate (78%)/propyl 1-[[2-(4-chloro-2,6-dimethylphenyl)acetyl]amino]-4,4-dipropoxycyclohexanecarboxylate (8%). The yield is 89%.

Example 19

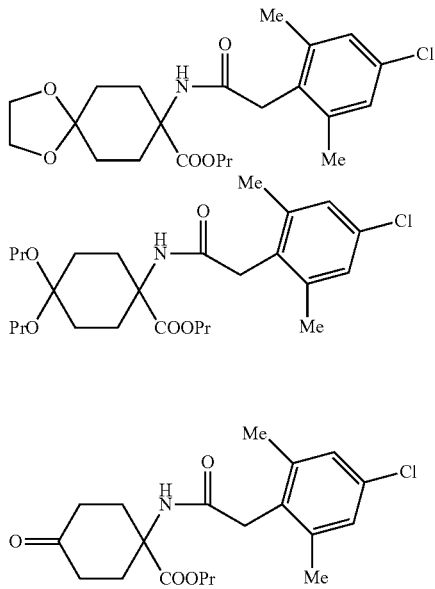

An initial charge of 227.8 g of the solution described in Example 15 is heated to 40° C., 400 g of toluene are added and incipient distillation is effected at reduced pressure down to 25 mbar. After 126.1 g of distillate have been removed, 400 g of toluene are added and a further 265.8 g of distillate are removed at 54-70 mbar. The vacuum is broken with nitrogen and the mixture is brought to standard pressure. The mixture is cooled down to 0-5° C. and a solution of 41.7 g of Na₂CO₃ in 208 g of water is metered in within 40 min. 128.5 g of 2-(4-chloro-2,6-dimethylphenyl)acetyl chloride (39.9% in toluene) are metered into the white suspension obtained at 0-5° C. within 2 h. On completion of metered addition, the mixture is heated to 77.4° C., the phases are separated from one another and the organic phase is concentrated on a rotary evaporator. This gives 100.6 g of a mixture of propyl 8-[[2-(4-chloro-2,6-dimethylphenyl)acetyl]amino]-1,4-dioxaspiro[4.5]decane-8-carboxylate (87%)/propyl 1-[[2-(4-chloro-2,6-dimethylphenyl)acetyl]amino]-4,4-dipropoxycyclohexanecarboxylate (1%)/propyl 1-[[2-(4-chloro-2,6-dimethylphenyl)acetyl]amino]-4-oxocyclohexanecarboxylate (9%). The yield is 99%.

Example 20

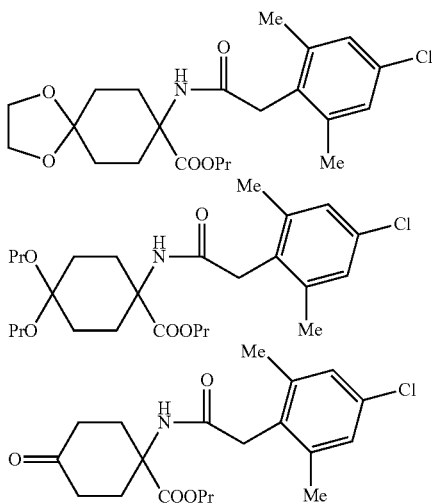

225.4 g of a solution that has been prepared analogously to Example 15 is incipiently distilled at internal temperature 25-30° C. and 25 mbar. After removal of 119.8 g of distillate, the vacuum is broken with nitrogen and the mixture is brought to standard pressure. 400 g of toluene are added and incipient distillation is repeated at 50-80 mbar. Toluene is constantly replenished during the distillation. In this way, a further 279.9 g of distillate were obtained and a total of 250 g of toluene were replenished. The mixture was then vented to standard pressure and cooled to 15-20° C. At this temperature, 41.4 g of Na$_2$CO$_3$ in 208.6 g of water are first metered in within 30 min, followed by dropwise addition of 128.5 g of 2-(4-chloro-2,6-dimethylphenyl)acetyl chloride (39.5% in toluene) within 90 min at such a rate that the temperature does not exceed 20° C. The mixture is stirred at 20° C. for a further 1 h and then heated to 78° C. The organic phase is removed and concentrated on a rotary evaporator. This gives 98.1 g of a pale yellow solid composed of propyl 8-[[2-(4-chloro-2,6-dimethylphenyl)acetyl]amino]-1,4-dioxaspiro[4.5]decane-8-carboxylate (87%)/propyl 1-[[2-(4-chloro-2,6-dimethylphenyl)acetyl]amino]-4,4-dipropoxycyclohexanecarboxylate (2%)/propyl 1-[[2-(4-chloro-2,6-dimethylphenyl)acetyl]amino]-4-oxocyclohexanecarboxylate (9%). The yield is 98%.

Example 21

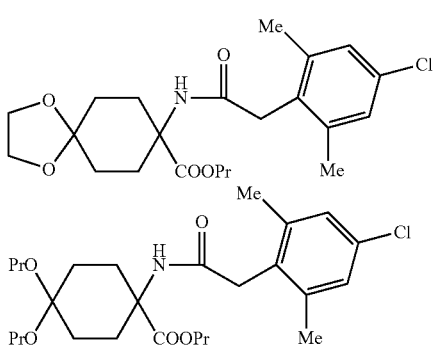

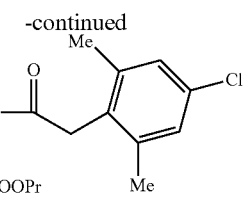

225.6 g of a solution that has been prepared analogously to Example 15 is incipiently distilled at internal temperature 30-40° C. and 25 mbar. After removal of 120.5 g of distillate, the vacuum is broken with nitrogen and the mixture is brought to standard pressure. 400 g of toluene are added and incipient distillation is repeated at 50-80 mbar. Toluene is constantly replenished during the distillation. In this way, a further 191.5 g of distillate are obtained and a total of 189 g of toluene are replenished. The mixture is vented to standard pressure and heated to 40° C. At this temperature, 41.4 g of Na$_2$CO$_3$ in 208.6 g of water are first metered in within 20 min followed by dropwise addition of 128.16 g of 2-(4-chloro-2,6-dimethylphenyl)acetyl chloride (39.5% in toluene) within 90 min at such a rate that the temperature does not exceed 40° C. The mixture is stirred at 40° C. for a further 15 min and then heated to 77° C. The organic phase is removed and concentrated on a rotary evaporator. This gives 101.92 g of a pale yellow solid composed of propyl 8-[[2-(4-chloro-2,6-dimethylphenyl)acetyl]amino]-1,4-dioxaspiro[4.5]decane-8-carboxylate (88%)/propyl 1-[[2-(4-chloro-2,6-dimethylphenyl)acetyl]amino]-4,4-dipropoxycyclohexanecarboxylate (7%)/propyl 1-[[2-(4-chloro-2,6-dimethylphenyl)acetyl]amino]-4-oxocyclohexanecarboxylate (3%). The yield is 99%.

Example 22

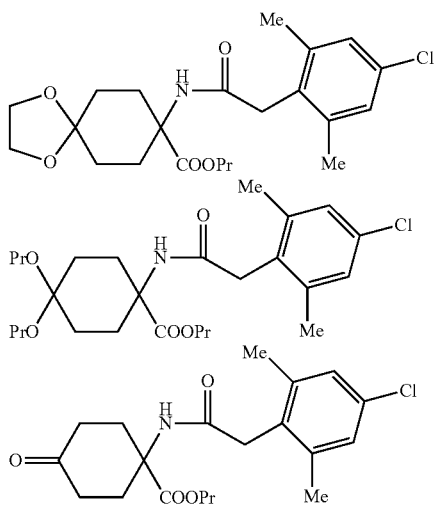

223.5 g of a solution that has been prepared analogously to Example 15 is incipiently distilled at internal temperature 30-40° C. and 25 mbar. After removal of 123.7 g of distillate, the vacuum is broken with nitrogen and the mixture is brought to standard pressure. 400 g of toluene are added and incipient distillation is repeated at 50-80 mbar. Toluene is constantly replenished during the distillation. In this way, a further 231.75 g of distillate are obtained and a total of 200 g of toluene are replenished. The mixture is then vented to standard pressure and heated to 40° C. At this temperature, 41.4 g of Na₂CO₃ in 208.6 g of water are first metered in within 20 min, followed by dropwise addition of 133.65 g of 2-(4-chloro-2,6-dimethylphenyl)acetyl chloride (39.5% in toluene) within 90 min at such a rate that the temperature does not exceed 40° C. The mixture is stirred at 40° C. for a further 15 min and then heated to 77° C. The organic phase is removed and concentrated on a rotary evaporator. This gives 103.4 g of a pale yellow solid composed of propyl 8-[[2-(4-chloro-2,6-dimethylphenyl)acetyl]amino]-1,4-dioxaspiro[4.5]decane-8-carboxylate (87%)/propyl 1-[[2-(4-chloro-2,6-dimethylphenyl)acetyl]amino]-4,4-dipropoxycyclohexanecarboxylate (1%)/propyl 1-[[2-(4-chloro-2,6-dimethylphenyl)acetyl]amino]-4-oxocyclohexanecarboxylate (8%). The yield is 98%.

Example 22a

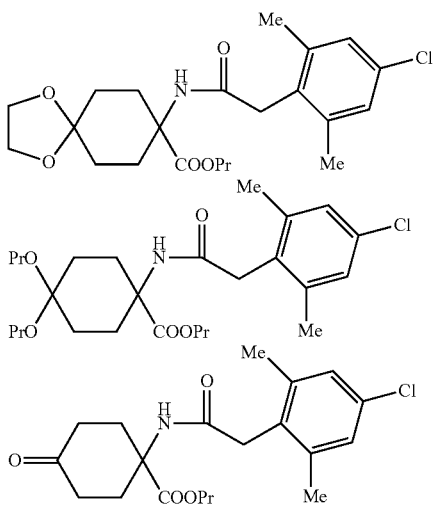

183.22 g of a solution that has been prepared analogously to Example 15 is incipiently distilled at internal temperature 30-40° C. and 25 mbar. After removal of 102.13 g of distillate, the vacuum is broken with nitrogen and the mixture is brought to standard pressure. 330 g of toluene are added, and the mixture is heated to 60° C. and incipiently distilled again at 100-300 mbar. Toluene is constantly replenished during the distillation. In this way, a further 127.5 g of distillate are obtained and a total of 107.6 g of toluene are replenished. The mixture was then vented to standard pressure and, at 60° C., 33.5 g of Na₂CO₃ in 171.3 g of water are first metered in within 20 min, followed by dropwise addition of 133.65 g of 2-(4-chloro-2,6-dimethylphenyl)acetyl chloride (39.5% in toluene) within 90 min at such a rate that the temperature does not exceed 60° C. The mixture is stirred at 40° C. for a further 15 min and then heated to 77° C. The organic phase is removed and concentrated on a rotary evaporator. This gives 84.5 g of a yellow solid composed of propyl 8-[[2-(4-chloro-2,6-dimethylphenyl)acetyl]amino]-1,4-dioxaspiro[4.5]decane-8-carboxylate (89%)/propyl 1-[[2-(4-chloro-2,6-dimethylphenyl)acetyl]amino]-4,4-dipropoxycyclohexanecarboxylate (0%)/propyl 1-[[2-(4-chloro-2,6-dimethylphenyl)acetyl]amino]-4-oxo-cyclohexanecarboxylate (7%). Yield 97%.

Example 23

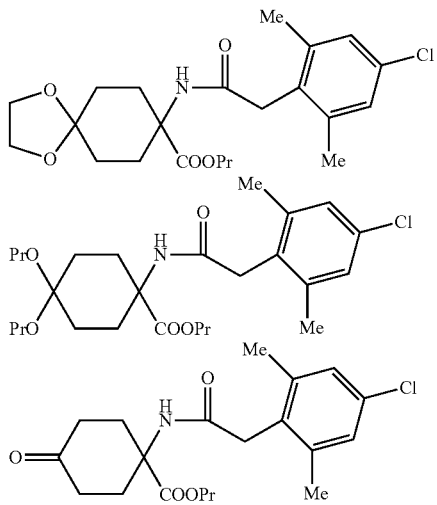

180.4 g of a solution that has been prepared analogously to Example 15 is incipiently distilled at internal temperature 30-40° C. and 25 mbar. After removal of 94.5 g of distillate, the vacuum is broken with nitrogen and the mixture is brought to standard pressure. 330 g of toluene are added, and the mixture is heated to 70-80° C. and incipiently distilled again at 300-400 mbar. Toluene is constantly replenished during the distillation. In this way, a further 100 g of distillate are obtained and a total of 69.9 g of toluene are replenished. The mixture was then vented to standard pressure and, at 60-80° C., 33.5 g of Na₂CO₃ in 171.3 g of water are first metered in within 20 min, followed by dropwise addition of 107.9 g of 2-(4-chloro-2,6-dimethylphenyl) acetyl chloride (39.5% in toluene) within 90 min at such a rate that the temperature does not exceed 80° C. The mixture is stirred at 80° C. for a further 15 min and then heated to 77° C. The organic phase is removed and concentrated on a rotary evaporator. This gives 81.9 g of a yellow solid composed of propyl 8-[[2-(4-chloro-2,6-dimethylphenyl) acetyl]amino]-1,4-dioxaspiro[4.5]decane-8-carboxylate (88%)/propyl 1-[[2-(4-chloro-2,6-dimethylphenyl)acetyl] amino]-4,4-dipropoxycyclohexanecarboxylate (0%)/propyl 1-[[2-(4-chloro-2,6-dimethylphenyl)acetyl]amino]-4-oxo-cyclohexanecarboxylate (6%). The yield is 93%.

Example 24

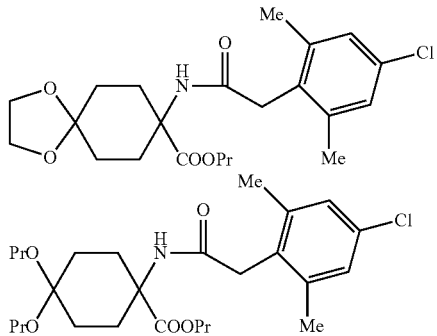

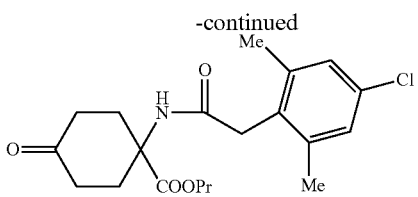

184.4 g of a solution that has been prepared analogously to Example 15 is incipiently distilled at internal temperature 30-40° C. and 25 mbar. After removal of 99.2 g of distillate, the vacuum is broken with nitrogen and the mixture is brought to standard pressure. 330 g of chlorobenzene are added, and the mixture is heated to 40° C. and incipiently distilled again down to 35 mbar. Chlorobenzene is constantly replenished during the distillation. In this way, a further 193.2 g of distillate are obtained and a total of 200 g of chlorobenzene are replenished. The mixture was then vented to standard pressure and, at 40° C., 33.7 g of $Na_2CO_3$ in 171.3 g of water are first metered in within 20 min, followed by dropwise addition of 109.6 g of 2-(4-chloro-2,6-dimethylphenyl)acetyl chloride (39.8% in toluene) within 90 min at such a rate that the temperature does not exceed 40° C. The mixture is stirred at 40° C. for a further 30 min and then heated to 75° C. The organic phase is removed and concentrated on a rotary evaporator. This gives 81.4 g of a yellow solid composed of propyl 8-[[2-(4-chloro-2,6-dimethylphenyl)acetyl]amino]-1,4-dioxaspiro[4.5]decane-8-carboxylate (86%)/propyl 1-[[2-(4-chloro-2,6-dimethylphenyl)acetyl]amino]-4,4-dipropoxycyclohexanecarboxylate (3%)/propyl 1-[[2-(4-chloro-2,6-dimethylphenyl)acetyl]amino]-4-oxocyclohexanecarboxylate (5%). The yield is 90%.

Example 25

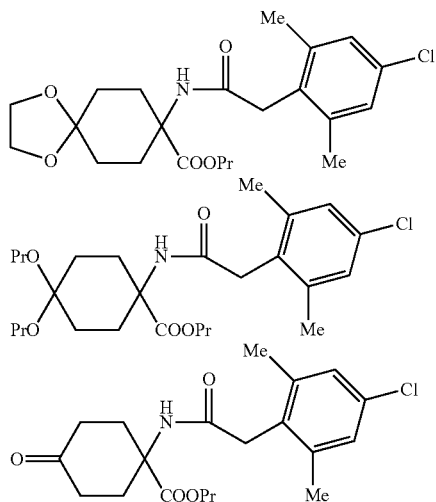

184.4 g of a solution that has been prepared analogously to Example 15 is incipiently distilled at internal temperature 30-40° C. and 25 mbar. After removal of 99.5 g of distillate, the vacuum is broken with nitrogen and the mixture is brought to standard pressure. 330 g of chlorobenzene are added, and the mixture is heated to 40° C. and incipiently distilled again down to 35 mbar. Chlorobenzene is constantly replenished during the distillation. In this way, a further 122 g of distillate are obtained and a total of 120 g of chlorobenzene are replenished. The mixture is then vented to standard pressure and, at 40° C., 33.7 g of $Na_2CO_3$ in 171.3 g of water are first metered in within 20 min, followed by dropwise addition of 111.9 g of 2-(4-chloro-2,6-dimethylphenyl)acetyl chloride (39.1% in chlorobenzene) within 90 min at such a rate that the temperature does not exceed 40° C. The mixture is stirred at 40° C. for a further 30 min and then heated to 75° C. The organic phase is removed and concentrated on a rotary evaporator. This gives 86.7 g of a yellow solid composed of propyl 8-[[2-(4-chloro-2,6-dimethylphenyl)acetyl]amino]-1,4-dioxaspiro[4.5]decane-8-carboxylate (82%)/propyl 1-[[2-(4-chloro-2,6-dimethylphenyl)acetyl]amino]-4,4-dipropoxycyclohexanecarboxylate (7%)/propyl 1-[[2-(4-chloro-2,6-dimethylphenyl)acetyl]amino]-4-oxocyclohexanecarboxylate (4%). The yield is 95%.

Example 26

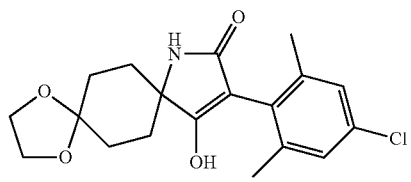 [SMILES: Cc1cc(Cl)cc(C)c1C1=C(O)C2(CCC3(CC2)OCCO3)NC1=O]

An initial charge of 60 g of 8-amino-1,4-dioxaspiro[4.5]decane-8-carboxylic acid in 196 g of 1-propanol is heated to 70-80° C. 39 g of thionyl chloride are added dropwise to the mixture within 30 minutes. Gas formed is removed via a scrubber containing sodium hydroxide solution. The mixture is stirred at 80-90° C. for a further 4 h. The mixture is cooled down to 45° C. and incipiently distilled under reduced pressure. This gives 120 g of distillate. 455 g of toluene are added to the distillation bottoms, and a further 164 g of distillate are removed. The mixture is cooled down to −5 to 5° C., and 50 g of sodium carbonate dissolved in 274 g of water are metered in within 40 min. Thereafter, 152.8 g of 2-(4-chloro-2,6-dimethylphenyl)acetyl chloride (40% in toluene) are metered in at such a rate that 5° C. is not exceeded. The suspension formed is heated to 70-80° C., the lower aqueous phase is removed, and the upper organic phase is washed once with 70 g of water at 80° C. 9 g of ethanediol and 2.8 g of 7% hydrochloric acid are added to the organic phase, and water is separated out of the mixture at 102-110° C. After 3 h, the toluene is distilled off, and the bottoms are taken up in 123 g of DMAc and incipiently distilled once again at about 100° C. under reduced pressure. 101.4 g of a 30% sodium methoxide solution are added to the remaining reaction mixture within one hour. Under slightly reduced pressure, methanol and propanol that are obtained continuously are distilled off. The mixture is stirred for a further 4 h, then 352 g of water are added and the mixture is stirred at 95° C. for a further 1 h. The solution is cooled down to 80° C. and 56 g of 37% hydrochloric acid are metered in. The mixture is cooled down to room temperature within 2 h, the suspension formed is filtered, and the filtercake is washed with 2×120 g of water and dried at 50° C. under reduced pressure. This gives 96 g of 2-(4-chloro-2,6-dimethylphenyl)-1-hydroxy-9,12-dioxa-4-azadispiro[4.2.4$^8$.2$^5$]tetradec-1-en-3-one with a purity of 94%. The yield is 88%.

Example 27

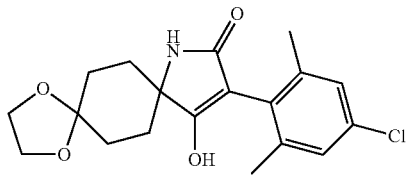 [SMILES: Cc1cc(Cl)cc(C)c1C1=C(O)C2(CCC3(CC2)OCCO3)NC1=O]

100 g of 8-amino-1,4-dioxaspiro[4.5]decane-8-carboxylic acid forms an initial charge in 319 g of 1-propanol. At 70-85° C., 63.2 g of thionyl chloride are metered in within one hour and then the mixture is stirred at 80-90° C. for a further 1 h. The mixture is cooled to 30° C. and incipiently distilled under reduced pressure at 30-50 mbar. This gives 130 g of distillate. 470 g of toluene are added, and a further 333 g of distillate are removed by incipient distillation again. The bottoms are cooled to −5 to 5° C., 87 g of Na$_2$CO$_3$ dissolved in 435 g of water are metered in within one hour, and then 265 g of 2-(4-chloro-2,6-dimethylphenyl)acetyl chloride are metered in as a 39.6% solution in toluene within 40 min. The mixture is stirred at room temperature for a further 1 h and heated to 80° C. After the lower aqueous phase has been removed, the remaining organic phase is washed with 50 g of water. Thereafter, 9.2 g of para-toluenesulfonic acid and 30 g of ethanediol are added, the mixture is heated to reflux and water is separated out for 3 h. The reaction mixture is then incipiently distilled (308 g of distillate), and 100 g of DMAc are added. The mixture is incipiently distilled again, and 15 g of distillate are removed. 135 g of sodium methoxide (30% solution in methanol) are metered into the remaining mixture at 110° C. within 30 min, and methanol and 1-propanol obtained under slightly reduced pressure are distilled off for 3 h. 235 g of water are added and the mixture is stirred at 90-100° C. for 1 h. Thereafter, the mixture is cooled to 80° C., then 46.4 g of acetic acid are added within 30 minutes, the mixture is cooled down to room temperature within 3 h, and the suspension formed is filtered off. The filtercake is washed with 2×150 g of water. This gives 165 g of 2-(4-chloro-2,6-dimethylphenyl)-1-hydroxy-9,12-dioxa-4-azadispiro[4.2.4$^8$.2$^5$]tetradec-1-en-3-one with a purity of 87%. The yield is 82%.

Example 28

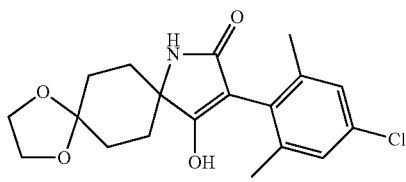 [SMILES: Cc1cc(Cl)cc(C)c1C1=C(O)C2(CCC3(CC2)OCCO3)NC1=O]

109 g of 8-amino-1,4-dioxaspiro[4.5]decane-8-carboxylic acid (96.9%) forms an initial charge in 357 g of 1-propanol. At 70-80° C., 71 g of thionyl chloride are metered in within 50 min and, after the metered addition has ended, the mixture is stirred for about a further 4 h. Incipient distillation is effected at maximum jacket temperature 45° C. and vacuum down to 23 mbar. After removal of 178 g of distillate, 830 g of toluene are added, a further 462 g of distillate are removed and the mixture is cooled to −5 to 5° C. 91 g of Na$_2$CO$_3$ in 500 g of water are added within one hour, followed by 280 g of 2-(4-chloro-2,6-dimethylphenyl)acetyl chloride (40% in toluene), likewise within 1 h. The mixture is heated to 80-90° C., the aqueous phase is removed, and the organic phase is admixed with 9 g of para-toluenesulfonic acid and 32 g of ethanediol. With a water separator attached, the mixture is refluxed at standard pressure for 5 h. The toluene is distilled off and the remaining bottoms are taken up in 224 g of DMAc. The mixture is incipiently distilled to a minor degree and 185 g of sodium methoxide (30% solution in methanol) are metered in at 100-120° C. Methanol and 1-propanol are distilled off at 100-120° C. under slightly reduced pressure over the course of 2 h. 600 g of water are added to the mixture, which is stirred at 85-100° C. for a further 1 h. The mixture is cooled down to 80° C., and 97 g of acetic acid are added within 30 min. Thereafter, the mixture is cooled down to room temperature, the suspension is filtered with suction and the filtercake is washed with 2×180 g of water. After drying under reduced pressure, this gives 171.5 g of 2-(4-chloro-2,6-dimethylphenyl)-1-hydroxy-9,12-dioxa-4-azadispiro[4.2.4$^8$.2$^5$]tetradec-1-en-3-one with 94% purity and 86% yield.

Example 29

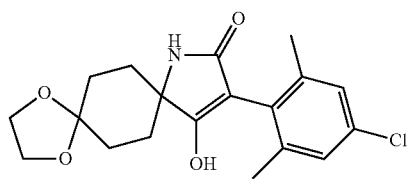 [SMILES: Cc1cc(Cl)cc(C)c1C1=C(O)C2(CCC3(CC2)OCCO3)NC1=O]

An initial charge of 60 g of 8-amino-1,4-dioxaspiro[4.5]decane-8-carboxylic acid in 130 g of 1-propanol and 140 g of chlorobenzene is heated to 70-80° C. 70 g of thionyl chloride are added dropwise to the mixture within 30 minutes. Gas formed is removed via a scrubber containing sodium hydroxide solution. The mixture is stirred at 80-90° C. for a further 12 h. The mixture is cooled down to 45° C. and incipiently distilled under reduced pressure. This gives 160 g of distillate. 50 g of sodium carbonate, dissolved in 274 g of water, are metered in within 40 min. Thereafter, 152.8 g of 2-(4-chloro-2,6-dimethylphenyl)acetyl chloride (40% in toluene) are metered in. The suspension formed is heated to 70-80° C., the lower aqueous phase is removed, and the upper organic phase is washed once with 150 g of water at 80° C. 9 g of ethanediol and 2.8 g of para-toluenesulfonic acid are added to the organic phase, and water is separated out of the mixture at 100-110° C. under slightly reduced pressure. After 2 h, a further 9 g of ethanediol are added and water is separated out for a further 4 h. Thereafter, at 110° C., 105 g of a 30% sodium methoxide solution are added within one hour. Under slightly reduced pressure, methanol and propanol that are obtained continuously are distilled off. The mixture is stirred for a further 4 h, then 325 g of water are added and the mixture is stirred at 95° C. for a further 1 h. The solution is cooled down to 80° C. and 43 g of acetic acid are metered in. The mixture is cooled down to room temperature over the course of several hours, the suspension formed is filtered, and the filtercake is washed with 2×60 g of water and dried at 50° C. under reduced pressure. This gives 87 g of 2-(4-chloro- 2,6-dimethylphenyl)-1-hydroxy-9,12-dioxa-4-azadispiro[4.2.4⁸25]tetradec-1-en-3-one with a purity of 89%. The yield is 77%.

The examples which follow proceed from the product mixture of propyl 8-[[2-(4-chloro-2,6-dimethylphenyl)acetyl]amino]-1,4-dioxaspiro[4.5]decane-8-carboxylate/propyl 1-[[2-(4-chloro-2,6-dimethylphenyl)acetyl]amino]-4,4-dipropoxycyclohexanecarboxylate/propyl 1-[[2-(4-chloro-2,6-dimethylphenyl)acetyl]amino]-4-oxocyclohexanecarboxylate, but, like Examples 26 to 29 as well, can likewise be conducted without any intermediate isolation commencing from 8-amino-1,4-dioxaspiro[4.5]decane-8-carboxylic acid or the corresponding sodium or potassium salts thereof.

Example 30

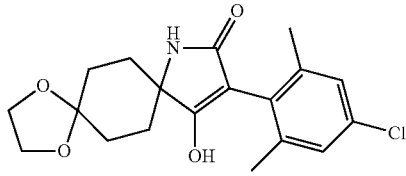

To 50 g of a mixture prepared analogously to Examples 15-25 in 116.7 g of chlorobenzene are added 1.5 g of 37% hydrochloric acid and 3.8 g of ethanediol, the mixture is heated to reflux, a further 1.5 g of hydrochloric acid are added after 4 h, and the mixture is stirred at reflux for a further 3 h. The mixture is cooled to 115° C., and 42.8 g of sodium methoxide (30% solution in methanol) are metered in under slightly reduced pressure within 30 min. Methanol and 1-propanol obtained are constantly distilled off for 2 h. 118 g of water are added to the mixture, which is stirred at 90-100° C. for 1 h. The mixture is cooled to 80° C., and 23.2 g of 37% hydrochloric acid are metered in within 30 min. The mixture is cooled down to room temperature over the course of several hours, another 50 g of water are added to the suspension formed in order to obtain stirrability, and then filtered. The filtercake is washed with 3×60 g of water. This gives 33.9 g of 2-(4-chloro-2,6-dimethylphenyl)-1-hydroxy-9,12-dioxa-4-azadispiro[4.2.4⁸.2⁵]tetradec-1-en-3-one with a purity of 95%. The yield is 87%, based on the mixture used.

Example 31

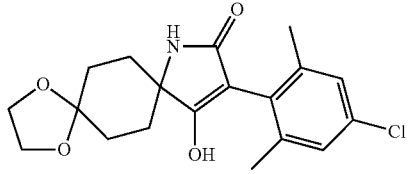 [SMILES: Cc1cc(Cl)cc(C)c1C1=C(O)C2(CCC3(CC2)OCCO3)NC1=O]

To 50 g of a mixture prepared analogously to Examples 15-25 in 116.7 g of chlorobenzene are added 1.5 g of 37% hydrochloric acid and 3.8 g of ethanediol, and the mixture is stirred at reflux with a water separator attached for 3 h. The chlorobenzene is incipiently distilled to a minor degree, 100 g of DMAc are added, and the chlorobenzene is distilled off at jacket temperature 130° C. under reduced pressure. At 94° C., 42.8 g of sodium methoxide are added to the mixture within 30 min, and 1-propanol and methanol are distilled off under slightly reduced pressure for 2 h. Then 118 g of water are added to the mixture, which is stirred at 90-100° C. for a further 1 h. The mixture is cooled to 80° C., and 23.2 g of 37% hydrochloric acid are added within 30 min. The mixture is cooled to 10° C. and filtered. The filtercake is washed with 60 g of water and dried under reduced pressure at 50° C. This gives 39.2 g of 2-(4-chloro-2,6-dimethylphenyl)-1-hydroxy-9,12-dioxa-4-azadispiro[4.2.4⁸.2⁵]tetradec-1-en-3-one with a purity of 90%. The yield is 95%, based on the mixture used.

Example 32

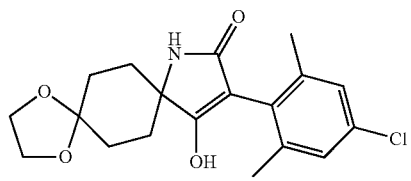 [SMILES: Cc1cc(Cl)cc(C)c1C1=C(O)C2(CCC3(CC2)OCCO3)NC1=O]

To 50 g of a mixture prepared analogously to Examples 15-25 in 116.7 g of anisole are added 5.3 g of para-toluenesulfonic acid and 6.5 g of ethanediol, and the mixture is stirred at reflux for 3 h. The mixture is cooled down to 115° C., and 42.8 g of sodium methoxide (30% solution in methanol) are metered in under slightly reduced pressure within 30 min. Methanol and 1-propanol obtained are constantly distilled off for 2 h. 118 g of water are added to the mixture, which is stirred at 90-100° C. for 1 h. The mixture is cooled to 80° C., and 20.8 g of acetic acid are metered in within 30 min. The mixture is cooled down to room temperature over the course of several hours and the suspension formed is filtered. The filtercake is washed with 2×60 g of water. This gives 35 g of 2-(4-chloro-2,6-dimethylphenyl)-1-hydroxy-9,12-dioxa-4-azadispiro[4.2.4⁸.2⁵]tetradec-1-en-3-one with a purity of 87%. The yield is 80%, based on the mixture used.

Example 33

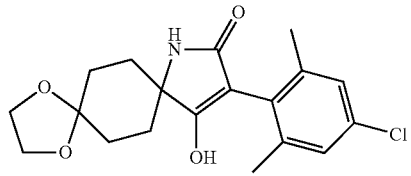 [SMILES: Cc1cc(Cl)cc(C)c1C1=C(O)C2(CCC3(CC2)OCCO3)NC1=O]

To 40 g of a mixture prepared analogously to Examples 15-25 and 115 g of toluene are added 1.5 g of para-toluenesulfonic acid and 5.4 g of ethanediol, the mixture is heated to reflux, the majority of the toluene is distilled off after 2 h, and 40 g of DMAc are added to the bottoms. ~8 g of distillate are removed from the mixture, which is cooled down to 115° C., and 28.1 g of sodium methoxide (30% solution in methanol) are metered in under slightly reduced pressure within 30 min. Methanol and 1-propanol obtained are constantly distilled off for 3 h. 95 g of water are added to the mixture, which is stirred at 90-100° C. for 1 h. The mixture is cooled to 80° C., and 19 g of acetic acid are metered in within 30 min. The mixture is cooled down to 10° C. over the course of 3 h, then the suspension formed is filtered. The filtercake is washed with 2×50 g of water. This gives 31.5 g of 2-(4-chloro-2,6-dimethylphenyl)-1-hydroxy-9,12-dioxa-4-azadispiro[4.2.4⁸.2⁵]tetradec-1-en-3-one with a purity of 97%. The yield is 91%, based on the mixture used.

Example 34

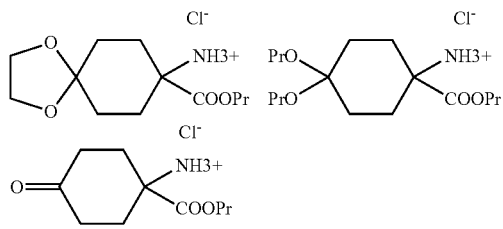

An initial charge of 50 g of 8-amino-1,4-dioxaspiro[4.5]decane-8-carboxylic acid in 59 g of 1-propanol and 100 g of toluene is heated to 80° C., and 29 g of thionyl chloride are metered into the mixture within one hour. After 5 h, the conversion check still indicates 20% reactant.

Example 35

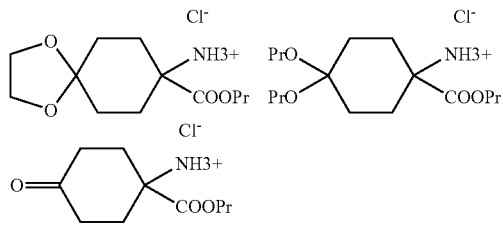

An initial charge of 60 g of 8-amino-1,4-dioxaspiro[4.5]decane-8-carboxylic acid in 86 g of 1-propanol and 120 g of chlorobenzene is heated to 80° C., and a sample is taken from the mixture: The conversion check indicates a ~25% reactant content. 39 g of thionyl chloride are metered into the mixture within one hour. After 5 h at 80-90° C., the conversion check shows ~11% w/w reactant. A further 15 g of thionyl chloride are added and the mixture is stirred at 80-90° C. for a further 5 h. Another conversion check shows 3.8% w/w reactant. Another 0.5 eq of thionyl chloride is added and the mixture is stirred at 80-90° C. for a further 4 h. The conversion check indicates 0.3% w/w reactant in the reaction mixture.

Example 36

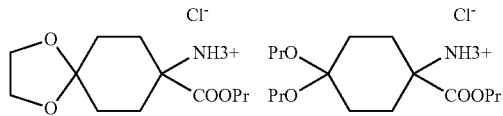

-continued

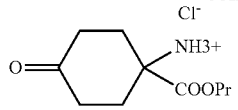

An initial charge of 51 g of 8-amino-1,4-dioxaspiro[4.5]decane-8-carboxylic acid in 101 g of 1-propanol is heated to 80° C., and a sample is taken from the mixture: A conversion check shows a 23% w/w reactant content. 28.9 g of thionyl chloride are metered into the mixture within one hour. After 5 h at 80-90° C., the conversion check shows 1.4% reactant in the reaction mixture.

Example 37

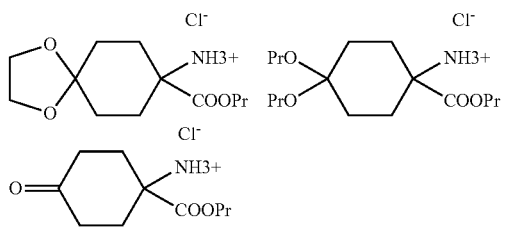

An initial charge of 50 g of sodium 8-amino-1,4-dioxaspiro[4.5]decane-8-carboxylate in 130 g of 1-propanol is heated to 80-90° C., and a sample is taken from the mixture: A conversion check shows ~23% w/w reactant. 46.9 g of thionyl chloride are metered into the mixture within one hour. After 5 h at 80-90° C., the conversion check shows 1.5% reactant in the reaction mixture.

Example 38

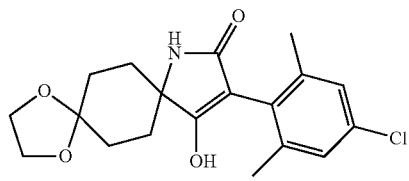 [SMILES: Cc1cc(Cl)cc(C)c1C1=C(O)C2(CCC3(CC2)OCCO3)NC1=O]

To 50 g of a mixture (about 0.081 mmol) prepared analogously to Examples 15-25 in 94 g of toluene are added 1 g of 96% sulfuric acid and 5.9 g of ethanediol, and the mixture is heated to reflux with a water separator attached. After 5 h, the majority of the toluene is distilled off and 50 g of DMAc are added. After another incipient distillation of the mixture, at 115° C., 34 g of sodium methoxide (30% solution in methanol) are metered in under slightly reduced pressure within 30 min. Methanol and 1-propanol obtained are constantly distilled off for 2 h. 95 g of water are added to the mixture, which is stirred at 90-100° C. for 1 h. The mixture is cooled to 80° C., and 11.3 g of acetic acid are metered in within 30 min. The mixture is cooled down to room temperature over the course of several hours, then the suspension formed is filtered. The filtercake is washed with 2×50 g of water. This gives 28.5 g of 2-(4-chloro-2,6-dimethylphenyl)-1-hydroxy-9,12-dioxa-4-azadispiro[4.2.48.25]tetradec-1-en-3-one with a purity of 94%. The yield is 90%, based on the mixture used.

The abbreviation "Pr" in the formula images stands for n-propyl.

The abbreviation "Bu" in the formula images stands for n-butyl.

The invention claimed is:

1. A process for preparing one or more compounds of formula (XI), comprising converting one or more compounds of formula (III) by reaction with one or more compounds of formula (XV)

$$R^7—OH \quad (XV)$$

and thionyl chloride to give one or more mixtures of one or more hydrochlorides of one or more compounds of formulae (IV'), (V') and (VI'), said one or more hydrochlorides are converted by one or more bases to one or more free compounds of formulae (IV'), (V') and (VI'), then said one or more free compounds are acylated in the presence of a base with one or more compounds of formula (VII) to obtain one or more mixtures of one or more compounds of formulae (VIII'), (IX') and (X'), then said one or more compounds of formulae (VIII'), (IX') and (X') are reacted in the presence of an acid with one or more compounds of formula (XIV)

$$HO—(CR^1R^2)_n—CR^3R^4—CR^5R^6—OH \quad (XIV)$$

to give one or more compounds of formula (XVI) and said one or more compounds of formula (XVI) are then cyclized in a Dieckmann reaction by the action of a strong base to give one or more compounds of formula (XI):

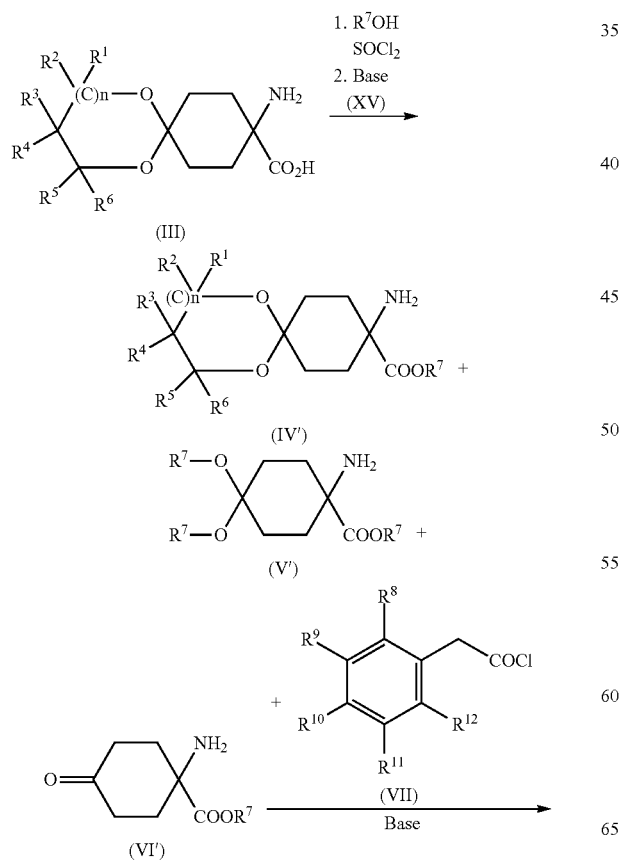

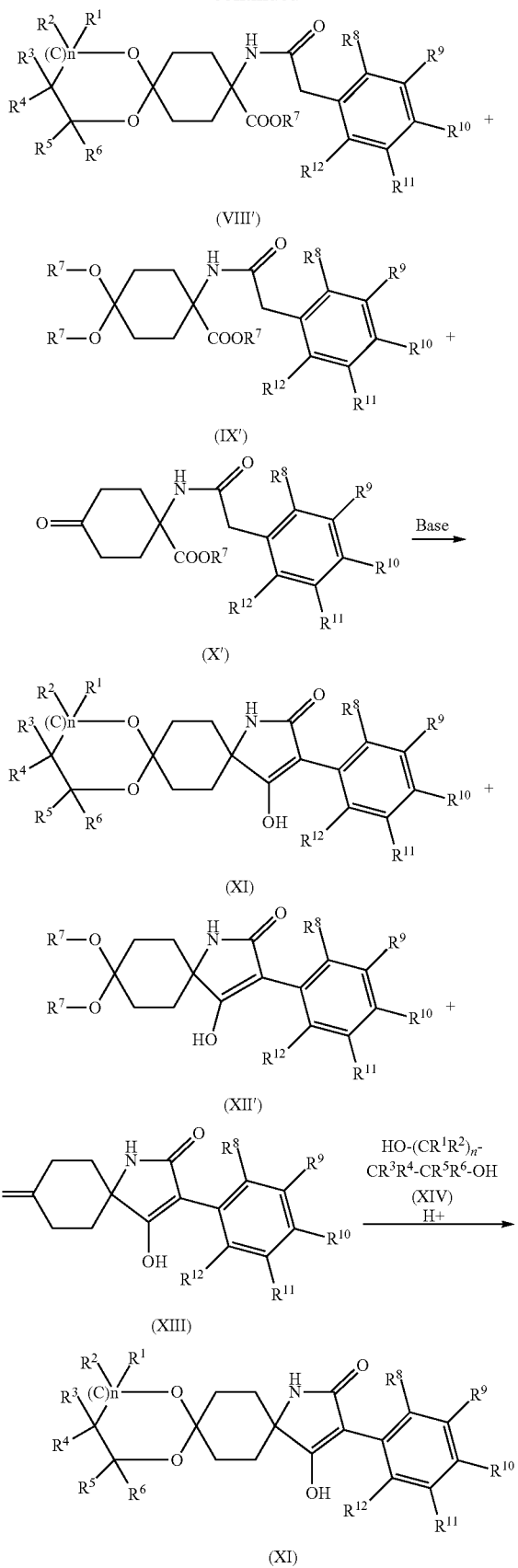

where
- $R^1$ to $R^6$ are independently hydrogen, methyl, ethyl or phenyl,
- $R^7$ is optionally branched $C_2$-$C_8$-alkyl,
- $R^8$ to $R^{12}$ are independently hydrogen, methyl, ethyl, fluoroalkyl having one or 2 carbon atoms and one to five fluorine atoms, halogen, methoxy, ethoxy, trifluoromethoxy or optionally methyl-, ethyl-, methoxy-, ethoxy- or halogen-substituted phenyl,
- $R^{13}$ is optionally branched $C_2$-$C_8$-alkyl or —$(CR^1R^2)_n$—$CR^3R^4$—$CR^5R^6$—OH, and
- n is 0 or 1.

2. Process according to claim 1, where
- $R^1$ to $R^6$ are independently hydrogen, methyl or ethyl,
- $R^7$ is ethyl, n-propyl, i-propyl, n-butyl or n-hexyl,
- $R^8$ to $R^{12}$ are independently hydrogen, methyl, ethyl, fluorine, chlorine, bromine, methoxy, ethoxy, trifluoromethoxy or optionally methyl-, ethyl-, methoxy-, ethoxy-, fluorine-, chlorine- or bromine-substituted phenyl,
- $R^{13}$ is ethyl, n-propyl, i-propyl, n-butyl, n-hexyl or —$(CR^1R^2)_n$—$CR^3R^4$—$CR^5R^6$—OH, and
- n is 0 or 1.

3. Process according to claim 1, where
- $R^3$ to $R^6$ are independently hydrogen or methyl,
- $R^7$ is ethyl, n-propyl, i-propyl, n-butyl or n-hexyl,
- $R^8$ to $R^{12}$ are independently hydrogen, methyl, ethyl, fluorine, chlorine, bromine, methoxy, ethoxy or optionally methyl-, methoxy-, fluorine- or chlorine-substituted phenyl,
- $R^{13}$ is ethyl, n-propyl, i-propyl, n-butyl, n-hexyl or —$(CR^1R^2)_n$—$CR^3R^4$—$CR^5R^6$—OH, and
- n is 0.

4. Process according to claim 1, where
- $R^3$ is hydrogen,
- $R^4$ is hydrogen or methyl,
- $R^5$ is hydrogen,
- $R^6$ is hydrogen or methyl,
- $R^7$ is ethyl, n-propyl, i-propyl, n-butyl or n-hexyl,
- $R^8$ is hydrogen, methyl, ethyl, methoxy, ethoxy, chlorine or bromine,
- $R^9$ is hydrogen,
- $R^{10}$ is hydrogen, methyl, chlorine or bromine,
- $R^{11}$ is hydrogen,
- $R^{12}$ is hydrogen, methyl, ethyl, methoxy, ethoxy, chlorine or bromine,
- $R^{13}$ is ethyl, n-propyl, i-propyl, n-butyl, n-hexyl or —$(CR^1R^2)_n$—$CR^3R^4$—$CR^5R^6$—OH, and
- n is 0.

5. Process according to claim 1, where
- $R^3$ is hydrogen,
- $R^4$ is hydrogen,
- $R^5$ is hydrogen,
- $R^6$ is hydrogen,
- $R^7$ is ethyl, n-propyl or n-butyl,
- $R^8$ is methyl, ethyl, chlorine or bromine,
- $R^9$ is hydrogen,
- $R^{10}$ is hydrogen, chlorine or bromine,
- $R^{11}$ is hydrogen,
- $R^{12}$ is methyl, ethyl, chlorine or bromine,
- $R^{13}$ is ethyl, n-propyl, i-propyl, n-butyl, n-hexyl or —$(CR^1R^2)_n$—$CR^3R^4$—$CR^5R^6$—OH, and
- n is 0.

6. Process according to claim 1, where
- $R^3$ is hydrogen,
- $R^4$ is hydrogen,
- $R^5$ is hydrogen,
- $R^6$ is hydrogen,
- $R^7$ is ethyl, n-propyl or n-butyl,
- $R^8$ is methyl,
- $R^9$ is hydrogen,
- $R^{10}$ is chlorine,
- $R^{11}$ is hydrogen,
- $R^{12}$ is methyl,
- $R^{13}$ is ethyl, n-propyl, i-propyl, n-butyl, n-hexyl or —$(CR^1R^2)_n$—$CR^3R^4$—$CR^5R^6$—OH, and
- n is 0.

7. Process according to claim 1, where
- $R^3$ is hydrogen,
- $R^4$ is hydrogen,
- $R^5$ is hydrogen,
- $R^6$ is hydrogen,
- $R^7$ is n-propyl,
- $R^8$ is methyl,
- $R^9$ is hydrogen,
- $R^{10}$ is chlorine,
- $R^{11}$ is hydrogen,
- $R^{12}$ is methyl,
- $R^{13}$ is n-propyl or —$CH_2CH_2$—OH, and
- n is 0.

* * * * *